(12) United States Patent
Hachigo et al.

(10) Patent No.: US 8,115,927 B2
(45) Date of Patent: Feb. 14, 2012

(54) PRODUCTION METHOD OF COMPOUND SEMICONDUCTOR MEMBER

(75) Inventors: Akihiro Hachigo, Itami (JP); Takayuki Nishiura, Itami (JP); Keiji Ishibashi, Itami (JP)

(73) Assignee: Sumitomo Electric Industries, Ltd., Osaka (JP)

(*) Notice: Subject to any disclaimer, the term of this patent is extended or adjusted under 35 U.S.C. 154(b) by 59 days.

(21) Appl. No.: 12/622,971

(22) Filed: Nov. 20, 2009

(65) Prior Publication Data
US 2010/0068834 A1 Mar. 18, 2010

Related U.S. Application Data

(63) Continuation of application No. 11/451,298, filed on Jun. 13, 2006, now abandoned.

(30) Foreign Application Priority Data

Jun. 13, 2005 (JP) ................. P2005-172567

(51) Int. Cl.
*G01J 4/00* (2006.01)
(52) U.S. Cl. ...................................... 356/369
(58) Field of Classification Search ............... None
See application file for complete search history.

(56) References Cited

U.S. PATENT DOCUMENTS

| 6,025,596 A * | 2/2000 | Shirai et al. ............ 250/339.11 |
| 2003/0127041 A1 | 7/2003 | Xu et al. |
| 2003/0157376 A1 | 8/2003 | Vaudo et al. |
| 2004/0207844 A1 * | 10/2004 | Nabatova-Gabain et al. ............ 356/369 |
| 2005/0012923 A1 * | 1/2005 | Shiba ............ 356/237.5 |
| 2007/0138465 A1 * | 6/2007 | Li ............ 257/48 |

FOREIGN PATENT DOCUMENTS

| CN | 1574242 | 2/2005 |
| JP | 11-087448 | 3/1999 |
| JP | 11-211655 A | 8/1999 |
| JP | 2001-230291 A | 8/2001 |
| JP | 2002-131136 A | 5/2002 |
| JP | 2003-224171 | 8/2003 |
| JP | 2005-033187 | 2/2005 |

OTHER PUBLICATIONS

Chinese Office Action, with English translation, issued in Chinese Patent Application No. 200610093021.8, dated Apr. 3, 2009.
Han S-H et al., "Effect of Cu deficiency on the defect levels of Cu0.86In1.09Se2.05 determined by spectroscopic ellipsometry," Applied Physics Letters, vol. 86, No. 2, Jan. 10, 2005, p. 021903-1- 021903-3.

(Continued)

*Primary Examiner* — Gregory J Toatley
*Assistant Examiner* — Juan D Valentin
(74) *Attorney, Agent, or Firm* — McDermott Will & Emery LLP

(57) ABSTRACT

A method of evaluating damage of a compound semiconductor member, comprising: a step of performing spectroscopic ellipsometry measurement on a surface of the compound semiconductor member; and a step of evaluating damage on the surface of the compound semiconductor member, using a spectrum in a wavelength band containing a wavelength corresponding to a bandgap of the compound semiconductor member, in a spectrum of an optical constant obtained by the spectroscopic ellipsometry measurement.

6 Claims, 25 Drawing Sheets

OTHER PUBLICATIONS

Joo H-Y et al., "Spectrophotometric analysis of aluminum nitride thin films," J. Vac. Sci. Technol. A, vol. 17, No. 3, May 1999, pp. 862-870.

Landheer D., et al., "Characterization of GaAs (110) Nitrided by an Electron-Cyclotron Resonance Plasma Source Using N2," Journal of the Electrochemical Society, vol. 147, No. 2, Feb. 2000, pp. 731-735.

Hikino S. et al., "Structural changes in ion-implanted and rapid thermally annealed Si(100) wafers studied by spectroscopic ellipsometry," Journal of Physics D: Applied Physics, vol. 37, No. 12, Jun. 21, 2004, pp. 1617-1623.

Japanese Notice of Reasons for Rejection, w/ English translation thereof, issued in Japanese Patent Application No. JP 2005-172567 dated Feb. 3, 2009.

European Search Report issued in European Patent Application No. EP 06009656.7 dated Nov. 2, 2011.

S. Peters et al., "In situ monitoring of GaN metal-organic vapor phase epitaxy by spectroscopic ellipsometry," Journal of Applied Physics, vol. 88, No. 7, Oct. 1, 2000.

K.A. Bell et al., "Systematic differences among nominal reference dielectric function spectra for crystalline Si as determined by he spectroscopic ellipsometry," Thin Solid Films 31-314 (1998) 161-166.

Y.-M. Xiong et al., "Variable angle spectroscopic ellipsometric characterization of surface damage in chemical-mechanical polished GaAs," Thin Solid Films, 220 (1992) 303-310.

H.W. Dinges et al., "Determination of ion beam etching damage on InP by spectroscopic ellipsometry," Applied Surface Science 50 (1991) 359-363.

P. Petrik et al., "Comparative study of ion implantation caused damage depth profiles in polycrystalline and single crystalline silicon studied by spectroscopic ellipsometry and Rutherford backscattering spectrometry," Nuclear Instruments and Methods in Physics Research B 147 (1999) 84-89.

P.K. Girt et al., "Crystalline to amorphous transition and band structure evolution in ion-damaged silicon studied by spectroscopic ellipsometry," Journal of Applied Physics, vol. 90, No. 2, Jul. 15, 2001.

V.G. Kechagias et al., "'Real-time' multiwavelength ellipsometry diagnostics for monitoring dry etching of Si and TiNx deposition," Thin Solid Films 364 (2000) 213-219.

* cited by examiner

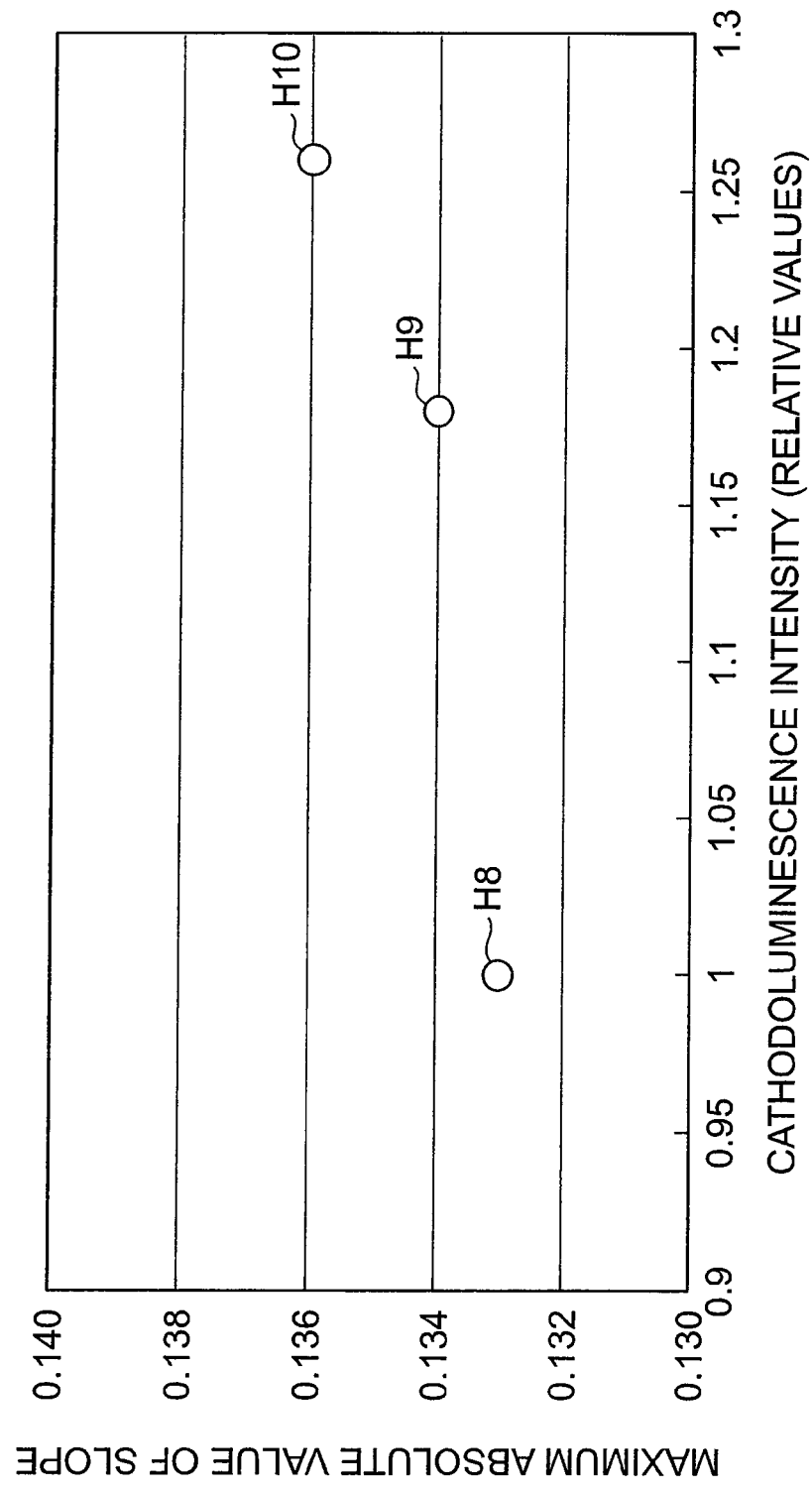

PRODUCTION METHOD OF COMPOUND SEMICONDUCTOR MEMBER

CROSS-REFERENCE TO RELATED APPLICATIONS

This application is a Continuation of U.S. application Ser. No. 11/451,298, filed on Jun. 13, 2006 now abandoned, claiming priority of Japanese Patent Application No. 2005-172567, filed on Jun. 13, 2005, the entire contents of which are hereby incorporated by reference.

BACKGROUND OF THE INVENTION

1. Field of the Invention

The present invention relates to a damage evaluation method of a compound semiconductor member, a production method of a compound semiconductor member, a gallium nitride compound semiconductor member, and a gallium nitride compound semiconductor membrane.

2. Related Background Art

Compound semiconductors have various merits in comparison with Si. For example, the compound semiconductors permit control of the bandgap through adjustment of compositions. Furthermore, the compound semiconductors have such optical properties as direct transition and wide bandgap, and are thus suitably applied to optical devices such as LEDs or LDs. Since the compound semiconductors have high carrier mobility, they are also suitably applied to high-speed devices.

In producing such compound semiconductor devices as the optical devices or high-speed devices, a substrate used is a compound semiconductor substrate, or a laminated substrate in which a compound semiconductor membrane is formed on an amorphous substrate such as a glass substrate. For example, a compound semiconductor membrane or electrodes are formed on a surface of the compound semiconductor substrate or laminated substrate. The device characteristics of the compound semiconductor devices are significantly affected by an interface between the compound semiconductor substrate or laminated substrate and the compound semiconductor membrane or by interfaces between the compound semiconductor substrate or laminated substrate and the electrodes. Therefore, it is important to evaluate the interfaces in the compound semiconductor devices.

In production of the compound semiconductor devices, damage occurs on the foregoing interfaces in several production processes. For example, since surface roughness of the compound semiconductor substrate or laminated substrate affects the device characteristics, the surface of the compound semiconductor substrate or laminated substrate is subjected to polishing or etching. This process produces scratches or distortion on the surface to cause damage on the surface. For example, dry etching or wet etching or the like is used in forming a thin film or fine pattern of nanometer size on the surface of the compound semiconductor substrate or laminated substrate. At this time; damage is caused on the surface of the compound semiconductor substrate or laminated substrate or on the surface of the thin film or fine pattern.

When a compound semiconductor device is produced, for example, by growing an epitaxial film on the surface of the compound semiconductor substrate or compound semiconductor membrane with the surface including the damage as described above, the device characteristics are degraded by virtue of the damage existing at the interface between the compound semiconductor substrate or compound semiconductor membrane and the epitaxial film.

Methods for evaluating the damage on the surface of the compound semiconductor substrate or compound semiconductor membrane include methods using X-ray diffraction, scanning electron microscope (SEM), cathodoluminescence, or the like as usually adopted methods.

On the other hand, Japanese Patent Application Laid-Open No. 11-87448 discloses a method of evaluating damage on a substrate by ellipsometry. This method is to evaluate a depth of a damage layer or a level of damage from a change rate of intensity of reflected light from the substrate.

Japanese Patent Application Laid-Open No. 2005-33187 discloses a method of subjecting a wafer to an etching treatment and evaluating a surface structure of the wafer after the etching treatment by ellipsometry. This method is to project polarized light onto the wafer and to evaluate the surface structure of the wafer, using polarized light reflected from the wafer. Specifically, the surface structure of the wafer is estimated from a phase difference $\Delta$ and an amplitude ratio $\psi$ between the polarized light projected onto the wafer and the polarized light reflected from the wafer.

SUMMARY OF THE INVENTION

However, the methods disclosed in the foregoing patent applications are not satisfactory yet in accuracy of damage evaluation on a surface of a compound semiconductor member, and there are desires for further improvement in the accuracy.

An object of the present invention is therefore to provide a damage evaluation method of a compound semiconductor member and a production method of a compound semiconductor member capable of evaluating a level of damage on a surface with high accuracy and to provide a gallium nitride compound semiconductor member and a gallium nitride compound semiconductor membrane with a low level of damage.

In order to solve the above problem, a damage evaluation method of a compound semiconductor member according to the present invention is (1) a method of evaluating damage of a compound semiconductor member, comprising: a step of performing spectroscopic ellipsometry measurement on a surface of the compound semiconductor member; and a step of evaluating damage on the surface of the compound semiconductor member, using a spectrum in a wavelength band containing a wavelength corresponding to a bandgap of the compound semiconductor member, in a spectrum of an optical constant obtained by the spectroscopic ellipsometry measurement. Here the term "spectrum of an optical constant" refers to data of an optical constant at wavelengths, for example.

Preferably, (2) the optical constant is an imaginary part of a complex index of refraction, and the step of evaluating the damage uses a maximum absolute value of a slope of the spectrum in the wavelength band.

Preferably, (3) the optical constant is an imaginary part of a complex index of refraction, and the step of evaluating the damage uses an absolute value of an extremum of a first derivative of the spectrum in the wavelength band.

Preferably, (4) the optical constant is an imaginary part of a complex index of refraction, and the step of evaluating the damage uses a wavelength at which an absolute value of a slope of the spectrum in the wavelength band is maximum.

Preferably, (5) the optical constant is an imaginary part of a complex index of refraction, and the step of evaluating the damage uses a maximum of the spectrum in the wavelength band.

Another damage evaluation method of a compound semiconductor member according to the present invention is (6) a method of evaluating damage of a compound semiconductor member, comprising: a step of performing spectroscopic ellipsometry measurement on a surface of the compound semiconductor member; and a step of evaluating damage on the surface of the compound semiconductor member, using a peak in a separate wavelength band located on a longer wavelength side than a wavelength band containing a wavelength corresponding to a bandgap of the compound semiconductor member, in a spectrum of an imaginary part of a complex index of refraction obtained by the spectroscopic ellipsometry measurement.

Still another damage evaluation method of a compound semiconductor member according to the present invention is (7) a method of evaluating damage of a compound semiconductor member, comprising: a step of performing spectroscopic ellipsometry measurement on a surface of a damage layer in the compound semiconductor member having a compound semiconductor region and the damage layer provided on the compound semiconductor region; and a step of evaluating damage on the surface of the damage layer in the compound semiconductor member, using a peak appearing in a spectrum of an imaginary part of a complex index of refraction with at least one reflection of light between the compound semiconductor region and the damage layer, in the spectrum of the imaginary part of the complex index of refraction obtained by the spectroscopic ellipsometry measurement.

Preferably, (8) the optical constant is an imaginary part of a complex dielectric constant, and the step of evaluating the damage uses a maximum absolute value of a slope of the spectrum in the wavelength band.

Preferably, (9) the optical constant is an imaginary part of a complex dielectric constant, and the step of evaluating the damage uses an absolute value of an extremum of a first derivative of the spectrum in the wavelength band.

Preferably, (10) the optical constant is an imaginary part of a complex dielectric constant, and the step of evaluating the damage uses a wavelength at which an absolute value of a slope of the spectrum in the wavelength band is maximum.

Preferably, (11) the optical constant is an imaginary part of a complex dielectric constant, and the step of evaluating the damage uses a maximum of the spectrum in the wavelength band.

Another damage evaluation method of a compound semiconductor member according to the present invention is (12) a method of evaluating damage of a compound semiconductor member, comprising: a step of performing spectroscopic ellipsometry measurement on a surface of the compound semiconductor member; and a step of evaluating damage on the surface of the compound semiconductor member, using a peak in a separate wavelength band located on a longer wavelength side than a wavelength band containing a wavelength corresponding to a bandgap of the compound semiconductor member, in a spectrum of an imaginary part of a complex dielectric constant obtained by the spectroscopic ellipsometry measurement.

Still another damage evaluation method of a compound semiconductor member according to the present invention is (13) a method of evaluating damage of a compound semiconductor member, comprising: a step of performing spectroscopic ellipsometry measurement on a surface of a damage layer in the compound semiconductor member having a compound semiconductor region and the damage layer provided on the compound semiconductor region; and a step of evaluating damage on the surface of the damage layer in the compound semiconductor member, using a peak appearing in a spectrum of an imaginary part of a complex dielectric constant with at least one reflection of light between the compound semiconductor region and the damage layer, in the spectrum of the imaginary part of the complex dielectric constant of refraction obtained by the spectroscopic ellipsometry measurement.

Preferably, (14) the optical constant is a real part of a complex index of refraction, and the step of evaluating the damage uses a maximum absolute value of a slope in a portion located on a shorter wavelength side than a wavelength corresponding to a maximum in the spectrum in the wavelength band.

Preferably, (15) the optical constant is a real part of a complex index of refraction, and the step of evaluating the damage uses a maximum absolute value of a slope in a portion located on a longer wavelength side than a wavelength corresponding to a maximum in the spectrum in the wavelength band.

Preferably, (16) the optical constant is a real part of a complex index of refraction, and the step of evaluating the damage uses a wavelength at which an absolute value of a slope in a portion located on a shorter wavelength side than a wavelength corresponding to a maximum in the spectrum in the wavelength band is maximum.

Preferably, (17) the optical constant is a real part of a complex index of refraction, and the step of evaluating the damage uses a maximum of the spectrum in the wavelength band.

Preferably, (18) the optical constant is a real part of a complex dielectric constant, and the step of evaluating the damage uses a maximum absolute value of a slope in a portion located on a shorter wavelength side than a wavelength corresponding to a maximum in the spectrum in the wavelength band.

Preferably, (19) the optical constant is a real part of a complex dielectric constant, and the step of evaluating the damage uses a maximum absolute value of a slope in a portion located on a longer wavelength side than a wavelength corresponding to a maximum in the spectrum in the wavelength band.

Preferably, (20) the optical constant is a real part of a complex dielectric constant, and the step of evaluating the damage uses a wavelength at which an absolute value of a slope in a portion located on a shorter wavelength side than a wavelength corresponding to a maximum in the spectrum in the wavelength band is maximum.

Preferably, (21) the optical constant is a real part of a complex dielectric constant, and the step of evaluating the damage uses a maximum of the spectrum in the wavelength band.

Preferably, (22) the compound semiconductor member is a compound semiconductor substrate. Preferably, (23) the compound semiconductor member is a compound semiconductor membrane provided on a substrate. Preferably, (24) the compound semiconductor member is comprised of a monocrystalline material or polycrystalline material. Preferably, (25) the bandgap is not less than $1.6 \times 10^{-19}$ J.

Preferably, (26) the compound semiconductor member is comprised of a nitride compound semiconductor containing at least one of B, Al, and Ga. Preferably, (27) the compound semiconductor member is comprised of an oxide compound semiconductor containing at least one of Be and Zn. Preferably, (28) the compound semiconductor member is comprised of a ZnSe compound semiconductor.

A production method of a compound semiconductor member according to the present invention is (29) a method of producing a compound semiconductor member, comprising: a step of performing spectroscopic ellipsometry measurement on a surface of the compound semiconductor member; and a step of determining that the compound semiconductor member is nondefective when a maximum absolute value of a slope of a spectrum in a wavelength band containing a wavelength corresponding to a bandgap of the compound semiconductor member, in a spectrum of an imaginary part of a complex index of refraction obtained by the spectroscopic ellipsometry measurement is not less than a predetermined threshold.

Another production method of a compound semiconductor member according to the present invention is (30) a method of producing a compound semiconductor member, comprising: a step of performing spectroscopic ellipsometry measurement on a surface of the compound semiconductor member; and a step of determining that the compound semiconductor member is nondefective when an absolute value of an extremum of a first derivative of a spectrum in a wavelength band containing a wavelength corresponding to a bandgap of the compound semiconductor member, in a spectrum of an imaginary part of a complex index of refraction obtained by the spectroscopic ellipsometry measurement is not less than a predetermined threshold.

Another production method of a compound semiconductor member according to the present invention is (31) a method of producing a compound semiconductor member, comprising: a step of performing spectroscopic ellipsometry measurement on a surface of the compound semiconductor member; and a step of determining that the compound semiconductor member is nondefective when a wavelength at which an absolute value of a slope of a spectrum in a wavelength band containing a wavelength corresponding to a bandgap of the compound semiconductor member, in a spectrum of an imaginary part of a complex index of refraction obtained by the spectroscopic ellipsometry measurement is maximum, is not less than a predetermined threshold.

Another production method of a compound semiconductor member according to the present invention is (32) a method of producing a compound semiconductor member, comprising: a step of performing spectroscopic ellipsometry measurement on a surface of the compound semiconductor member; and a step of determining that the compound semiconductor member is nondefective when a maximum absolute value of a slope of a spectrum in a wavelength band containing a wavelength corresponding to a bandgap of the compound semiconductor member, in a spectrum of an imaginary part of a complex dielectric constant obtained by the spectroscopic ellipsometry measurement is not less than a predetermined threshold.

Still another production method of a compound semiconductor member according to the present invention is (33) a method of producing a compound semiconductor member, comprising: a step of performing spectroscopic ellipsometry measurement on a surface of the compound semiconductor member; and a step of determining that the compound semiconductor member is nondefective when an absolute value of an extremum of a first derivative of a spectrum in a wavelength band containing a wavelength corresponding to a bandgap of the compound semiconductor member, in a spectrum of an imaginary part of a complex dielectric constant obtained by the spectroscopic ellipsometry measurement is not less than a predetermined threshold.

Another production method of a compound semiconductor member according to the present invention is (34) a method of producing a compound semiconductor member, comprising: a step of performing spectroscopic ellipsometry measurement on a surface of the compound semiconductor member; and a step of determining that the compound semiconductor member is nondefective when a wavelength at which an absolute value of a slope of a spectrum in a wavelength band containing a wavelength corresponding to a bandgap of the compound semiconductor member, in a spectrum of an imaginary part of a complex dielectric constant obtained by the spectroscopic ellipsometry measurement is maximum, is not less than a predetermined threshold.

Another production method of a compound semiconductor member according to the present invention is (35) a method of producing a compound semiconductor member, comprising: a step of performing spectroscopic ellipsometry measurement on a surface of the compound semiconductor member; and a step of determining that the compound semiconductor member is nondefective when a maximum absolute value of a slope in a portion located on a shorter wavelength side than a wavelength corresponding to a maximum of a spectrum in a wavelength band containing a wavelength corresponding to a bandgap of the compound semiconductor member, in a spectrum of a real part of a complex index of refraction obtained by the spectroscopic ellipsometry measurement is not less than a predetermined threshold.

Another production method of a compound semiconductor member according to the present invention is (36) a method of producing a compound semiconductor member, comprising: a step of performing spectroscopic ellipsometry measurement on a surface of the compound semiconductor member; and a step of determining that the compound semiconductor member is nondefective when a maximum absolute value of a slope in a portion located on a longer wavelength side than a wavelength corresponding to a maximum of a spectrum in a wavelength band containing a wavelength corresponding to a bandgap of the compound semiconductor member, in a spectrum of a real part of a complex index of refraction obtained by the spectroscopic ellipsometry measurement is not less than a predetermined threshold.

Another production method of a compound semiconductor member according to the present invention is (37) a method of producing a compound semiconductor member, comprising: a step of performing spectroscopic ellipsometry measurement on a surface of the compound semiconductor member; and a step of determining that the compound semiconductor member is nondefective when a wavelength at which an absolute value of a slope in a portion located on a shorter wavelength side than a wavelength corresponding to a maximum in a spectrum in a wavelength band containing a wavelength corresponding to a bandgap of the compound semiconductor member, in a spectrum of a real part of a complex index of refraction obtained by the spectroscopic ellipsometry measurement is maximum, is not less than a predetermined threshold.

Another production method of a compound semiconductor member according to the present invention is (38) a method of producing a compound semiconductor member, comprising: a step of performing spectroscopic ellipsometry measurement on a surface of the compound semiconductor member; and a step of determining that the compound semiconductor member is nondefective when a maximum of a spectrum in a wavelength band containing a wavelength corresponding to a bandgap of the compound semiconductor member, in a spectrum of a real part of a complex index of refraction obtained by the spectroscopic ellipsometry measurement is not less than a predetermined threshold.

Another production method of a compound semiconductor member according to the present invention is (39) a method of producing a compound semiconductor member, comprising:

a step of performing spectroscopic ellipsometry measurement on a surface of the compound semiconductor member; and a step of determining that the compound semiconductor member is nondefective when a maximum absolute value of a slope in a portion located on a shorter wavelength side than a wavelength corresponding to a maximum of a spectrum in a wavelength band containing a wavelength corresponding to a bandgap of the compound semiconductor member, in a spectrum of a real part of a complex dielectric constant obtained by the spectroscopic ellipsometry measurement is not less than a predetermined threshold.

Another production method of a compound semiconductor member according to the present invention is (40) a method of producing a compound semiconductor member, comprising: a step of performing spectroscopic ellipsometry measurement on a surface of the compound semiconductor member; and a step of determining that the compound semiconductor member is nondefective when a maximum absolute value of a slope in a portion located on a longer wavelength side than a wavelength corresponding to a maximum of a spectrum in a wavelength band containing a wavelength corresponding to a bandgap of the compound semiconductor member, in a spectrum of a real part of a complex dielectric constant obtained by the spectroscopic ellipsometry measurement is not less than a predetermined threshold.

Another production method of a compound semiconductor member according to the present invention is (41) a method of producing a compound semiconductor member, comprising: a step of performing spectroscopic ellipsometry measurement on a surface of the compound semiconductor member; and a step of determining that the compound semiconductor member is nondefective when a wavelength at which an absolute value of a slope in a portion located on a shorter wavelength side than a wavelength corresponding to a maximum of a spectrum in a wavelength band containing a wavelength corresponding to a bandgap of the compound semiconductor member, in a spectrum of a real part of a complex dielectric constant obtained by the spectroscopic ellipsometry measurement is maximum, is not less than a predetermined threshold.

Another production method of a compound semiconductor member according to the present invention is (42) a method of producing a compound semiconductor member, comprising: a step of performing spectroscopic ellipsometry measurement on a surface of the compound semiconductor member; and a step of determining that the compound semiconductor member is nondefective when a maximum of a spectrum in a wavelength band containing a wavelength corresponding to a bandgap of the compound semiconductor member, in a spectrum of a real part of a complex dielectric constant obtained by the spectroscopic ellipsometry measurement is not less than a predetermined threshold.

Preferably, (43) the compound semiconductor member is a compound semiconductor substrate. Preferably, (44) the compound semiconductor member is a compound semiconductor membrane provided on a substrate.

Preferably, the production method of the compound semiconductor member further comprises (45) a step of forming a thin film on the surface of the compound semiconductor member, after the step of determining that the compound semiconductor member is nondefective.

Preferably, the production method of the compound semiconductor member further comprises (46) a step of forming an electrode on the surface of the compound semiconductor member, after the step of determining that the compound semiconductor member is nondefective.

A gallium nitride compound semiconductor member according to the present invention is (47) a gallium nitride compound semiconductor member wherein an absolute value of a difference between an imaginary part of a complex index of refraction at 360 nm and an imaginary part of a complex index of refraction at 370 nm obtained by spectroscopic ellipsometry measurement on a surface is not less than 0.045.

Another gallium nitride compound semiconductor member according to the present invention is (48) a gallium nitride compound semiconductor member wherein an absolute value of an imaginary part of a complex index of refraction at 370 nm obtained by spectroscopic ellipsometry measurement on a surface of the gallium nitride compound semiconductor member is not more than 0.18.

Still another gallium nitride compound semiconductor member according to the present invention is (49) a gallium nitride compound semiconductor member wherein in a spectrum of an imaginary part of a complex index of refraction obtained by spectroscopic ellipsometry measurement on a surface of the gallium nitride compound semiconductor member, a wavelength at which an absolute value of a slope of a spectrum in a wavelength band of 300 to 400 nm is maximum, is not less than 350 nm.

Still another gallium nitride compound semiconductor member according to the present invention is (50) a gallium nitride compound semiconductor member wherein an absolute value of a difference between an imaginary part of a complex dielectric constant at 360 nm and an imaginary part of a complex dielectric constant at 370 nm obtained by spectroscopic ellipsometry measurement on a surface of the gallium nitride compound semiconductor member is not less than 0.24.

Still another gallium nitride compound semiconductor member according to the present invention is (51) a gallium nitride compound semiconductor member wherein an absolute value of an imaginary part of a complex dielectric constant at 370 nm obtained by spectroscopic ellipsometry measurement on a surface of the gallium nitride compound semiconductor member is not more than 0.9.

Still another gallium nitride compound semiconductor member according to the present invention is (52) a gallium nitride compound semiconductor member wherein in a spectrum of an imaginary part of a complex dielectric constant obtained by spectroscopic ellipsometry measurement on a surface of the gallium nitride compound semiconductor member, a wavelength at which an absolute value of a slope of a spectrum in a wavelength band of 300 to 400 nm is maximum, is not less than 350 nm.

Still another gallium nitride compound semiconductor member according to the present invention is (53) a gallium nitride compound semiconductor member wherein an absolute value of a difference between a real part of a complex index of refraction at 365 nm and a real part of a complex index of refraction at 375 nm obtained by spectroscopic ellipsometry measurement on a surface of the gallium nitride compound semiconductor member is not less than 0.035.

Still another gallium nitride compound semiconductor member according to the present invention is (54) a gallium nitride compound semiconductor member wherein in a spectrum of a real part of a complex index of refraction obtained by spectroscopic ellipsometry measurement on a surface of the gallium nitride compound semiconductor member, a maximum of a spectrum in a wavelength band of 300 to 400 nm is not less than 2.7.

Still another gallium nitride compound semiconductor member according to the present invention is (55) a gallium nitride compound semiconductor member wherein an absolute value of a difference between a real part of a complex dielectric constant at 365 nm and a real part of a complex dielectric constant at 375 nm obtained by spectroscopic ellipsometry measurement on a surface of the gallium nitride compound semiconductor member is not less than 0.13.

Still another gallium nitride compound semiconductor member according to the present invention is (56) a gallium nitride compound semiconductor member wherein in a spectrum of a real part of a complex dielectric constant obtained by spectroscopic ellipsometry measurement on a surface of the gallium nitride compound semiconductor member, a maximum of a spectrum in a wavelength band of 300 to 400 nm is not less than 7.2.

Still another gallium nitride compound semiconductor member according to the present invention is (57) a gallium nitride compound semiconductor member wherein a thickness of a layer containing at least one of an oxide film and an uneven layer formed on a surface of the gallium nitride compound semiconductor member is not more than 6 nm.

Preferably, (58) the gallium nitride compound semiconductor member is a gallium nitride compound semiconductor substrate. Preferably, (59) the gallium nitride compound semiconductor member is a gallium nitride compound semiconductor membrane provided on a substrate.

A gallium nitride compound semiconductor membrane according to the present invention is (60) a gallium nitride compound semiconductor membrane formed on a gallium nitride compound semiconductor member wherein an absolute value of a difference between an imaginary part of a complex index of refraction at 360 nm and an imaginary part of a complex index of refraction at 370 nm obtained by spectroscopic ellipsometry measurement on a surface of the gallium nitride compound semiconductor member is not less than 0.045.

Another gallium nitride compound semiconductor membrane according to the present invention is (61) a gallium nitride compound semiconductor membrane formed on a gallium nitride compound semiconductor member wherein an absolute value of an imaginary part of a complex index of refraction at 370 nm obtained by spectroscopic ellipsometry measurement on a surface of the gallium nitride compound semiconductor member is not more than 0.18.

Still another gallium nitride compound semiconductor membrane according to the present invention is (62) a gallium nitride compound semiconductor membrane formed on a gallium nitride compound semiconductor member wherein in a spectrum of an imaginary part of a complex index of refraction obtained by spectroscopic ellipsometry measurement on a surface of the gallium nitride compound semiconductor member, a wavelength at which an absolute value of a slope of a spectrum in a wavelength band of 300 to 400 nm is maximum, is not less than 350 nm.

Still another gallium nitride compound semiconductor membrane according to the present invention is (63) a gallium nitride compound semiconductor membrane formed on a gallium nitride compound semiconductor member wherein an absolute value of a difference between an imaginary part of a complex dielectric constant at 360 nm and an imaginary part of a complex dielectric constant at 370 nm obtained by spectroscopic ellipsometry measurement on a surface of the gallium nitride compound semiconductor member is not less than 0.24.

Still another gallium nitride compound semiconductor membrane according to the present invention is (64) a gallium nitride compound semiconductor membrane formed on a gallium nitride compound semiconductor member wherein an absolute value of an imaginary part of a complex dielectric constant at 370 nm obtained by spectroscopic ellipsometry measurement on a surface of the gallium nitride compound semiconductor member is not more than 0.9.

Still another gallium nitride compound semiconductor membrane according to the present invention is (65) a gallium nitride compound semiconductor membrane formed on a gallium nitride compound semiconductor member wherein in a spectrum of an imaginary part of a complex dielectric constant obtained by spectroscopic ellipsometry measurement on a surface of the gallium nitride compound semiconductor member, a wavelength at which an absolute value of a slope of a spectrum in a wavelength band of 300 to 400 nm is maximum, is not less than 350 nm.

Still another gallium nitride compound semiconductor membrane according to the present invention is (66) a gallium nitride compound semiconductor membrane formed on a gallium nitride compound semiconductor member wherein an absolute value of a difference between a real part of a complex index of refraction at 365 nm and a real part of a complex index of refraction at 375 nm obtained by spectroscopic ellipsometry measurement on a surface of the gallium nitride compound semiconductor member is not less than 0.035.

Still another gallium nitride compound semiconductor membrane according to the present invention is (67) a gallium nitride compound semiconductor membrane formed on a gallium nitride compound semiconductor member wherein in a spectrum of a real part of a complex index of refraction obtained by spectroscopic ellipsometry measurement on a surface of the gallium nitride compound semiconductor member, a maximum of a spectrum in a wavelength band of 300 to 400 nm is not less than 2.7.

Still another gallium nitride compound semiconductor membrane according to the present invention is (68) a gallium nitride compound semiconductor membrane formed on a gallium nitride compound semiconductor member wherein an absolute value of a difference between a real part of a complex dielectric constant at 365 nm and a real part of a complex dielectric constant at 375 nm obtained by spectroscopic ellipsometry measurement on a surface of the gallium nitride compound semiconductor member is not less than 0.13.

Still another gallium nitride compound semiconductor membrane according to the present invention is (69) a gallium nitride compound semiconductor membrane formed on a gallium nitride compound semiconductor member wherein in a spectrum of a real part of a complex dielectric constant obtained by spectroscopic ellipsometry measurement on a surface of the gallium nitride compound semiconductor member, a maximum of a spectrum in a wavelength band of 300 to 400 nm is not less than 7.2.

Still another gallium nitride compound semiconductor membrane according to the present invention is (70) a gallium nitride compound semiconductor membrane formed on a gallium nitride compound semiconductor member wherein a thickness of a layer containing at least one of an oxide film and an uneven layer formed on a surface of the gallium nitride compound semiconductor member is not more than 6 nm.

BRIEF DESCRIPTION OF THE DRAWINGS

FIG. 25 is a graph showing a relation between cathodoluminescence intensities and maximum absolute values of slopes.

DESCRIPTION OF THE PREFERRED EMBODIMENTS

Embodiments of the present invention will be described below in detail with reference to the accompanying drawings. In the description of the drawings identical or equivalent elements will be denoted by the same reference symbols, without redundant description.

Figure 1:
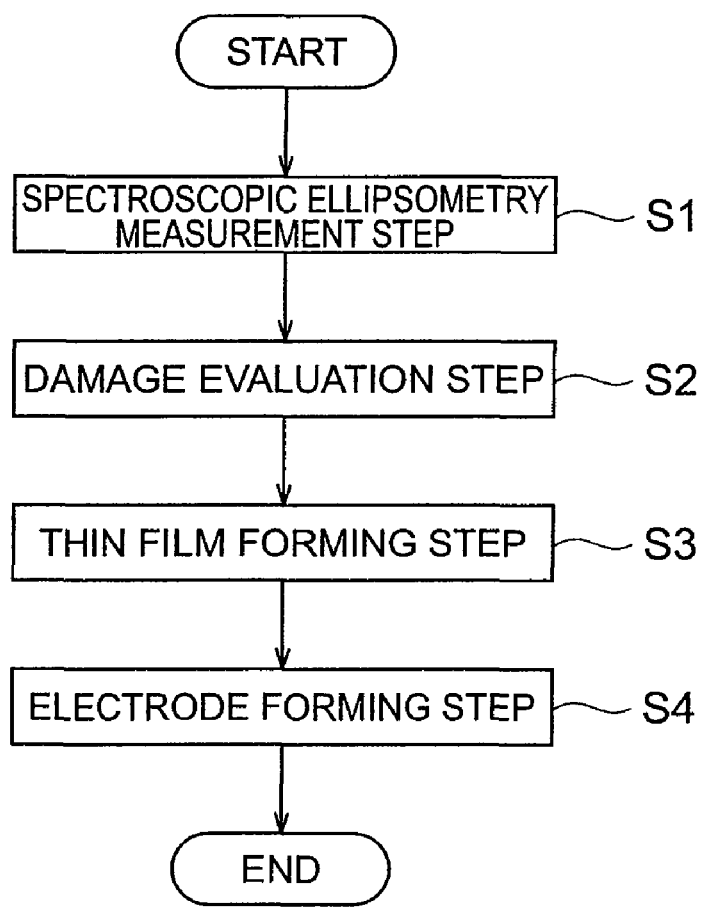
FIG. 1 is a flowchart showing steps in a damage evaluation method of a compound semiconductor member and in a production method of a compound semiconductor member according to an embodiment.

FIG. 1 is a flowchart showing steps in a damage evaluation method of a compound semiconductor member and in a production method of a compound semiconductor member according to an embodiment. The damage evaluation method of the compound semiconductor member according to the embodiment includes a spectroscopic ellipsometry measurement step S1 and a damage evaluation step S2. The production method of the compound semiconductor member according to the embodiment includes the spectroscopic ellipsometry measurement step S1 and the damage evaluation step S2 and, preferably, further includes a thin film forming step S3 and an electrode forming step S4.

(Spectroscopic Ellipsometry Measurement Step)

Figure 2:
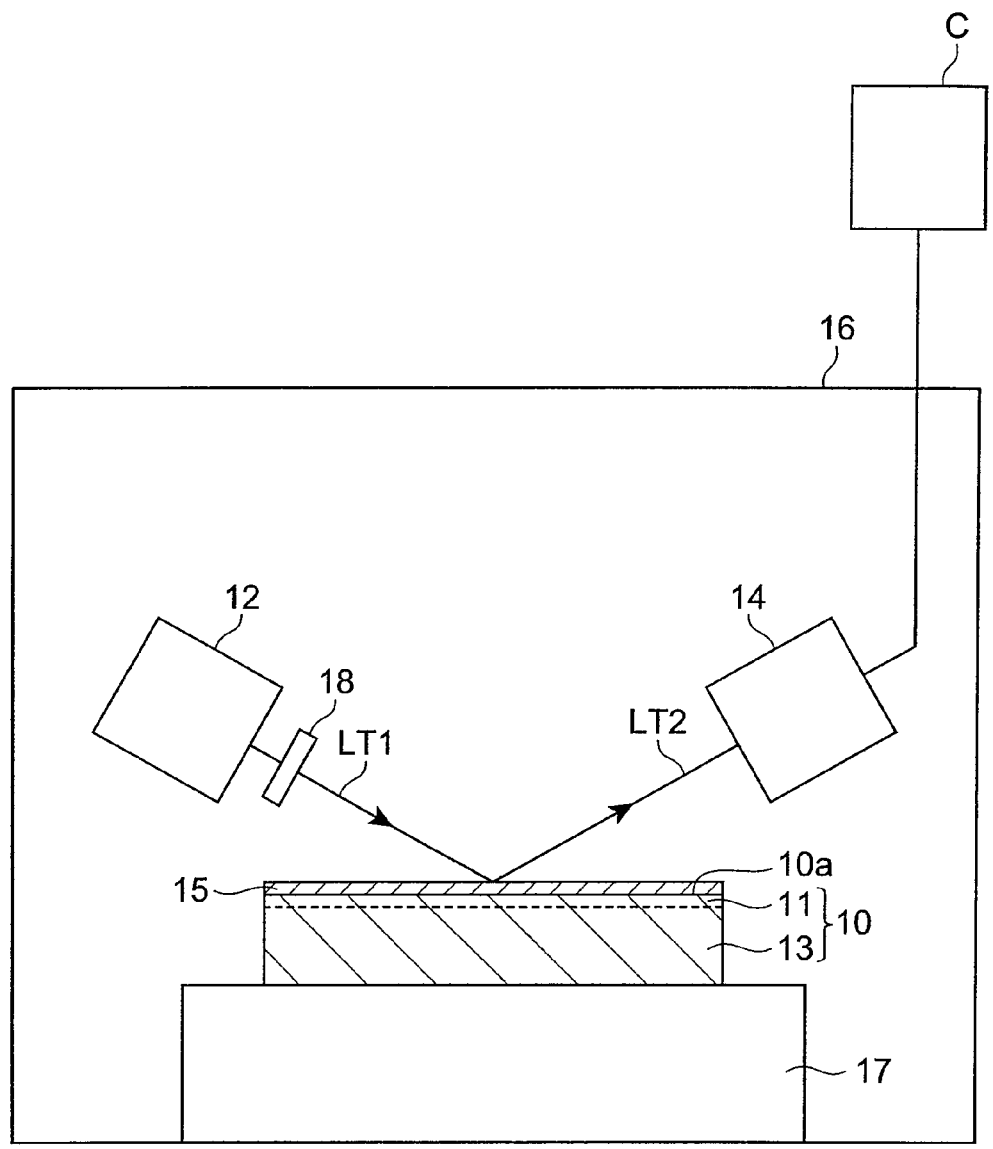
FIG. 2 is an illustration schematically showing a spectroscopic ellipsometry measurement step.

FIG. 2 is an illustration schematically showing the spectroscopic ellipsometry measurement step. The spectroscopic ellipsometry measurement step S1 is to perform spectroscopic ellipsometry measurement on a surface 10a of a compound semiconductor substrate 10 (compound semiconductor member). The spectroscopic ellipsometry measurement is carried out preferably with a spectroscopic ellipsometer 16.

The spectroscopic ellipsometer 16 has a stage 17 for supporting the compound semiconductor substrate 10, and a light source 12 for emitting light LT1 toward the surface 10a of the compound semiconductor substrate 10. The wavelength of light LT1 may be fixed or variable. The light LT1 emitted from the light source 12 is guided through a filter 18 to be converted into linearly polarized light. Therefore, the linearly polarized light LT1 is incident to the surface 10a of the compound semiconductor substrate 10. Light LT2 reflected on the surface 10a is incident to a light detection unit 14. A computer C is connected through an optical system (not shown) for measuring the amplitude ratio ψ and phase difference Δ of light LT2 as described later, to the light detection unit 14. The computer C saves the data of amplitude ratio ψ and phase difference Δ. The spectroscopic ellipsometer 16 is preferably provided with an angle adjusting mechanism (not shown) capable of manually or automatically adjusting the angle of incidence of the light LT1 and the angle of reflection of the light LT2 relative to the surface 10a.

The spectroscopic ellipsometry measurement is carried out well by use of the spectroscopic ellipsometer 16. First, initial adjustment of the spectroscopic ellipsometer 16 is carried out according to need. Specifically, for example, the compound semiconductor substrate 10 is mounted on the stage 17, and thereafter, while reference light is projected from the direction perpendicular to the surface 10a, onto the compound semiconductor substrate 10, the inclination of stage 17 is adjusted so as to match the reference light with its reflected light. Subsequently, the light LT1 is projected from a direction shifted by a predetermined angle from the direction perpendicular to the surface 10a, onto the compound semiconductor substrate 10, and the light source 12 and light detection unit 14 are set at a predetermined angle of incidence by adjusting the distance between the light source 12 and the compound semiconductor substrate 10, the angle of incidence of the light LT1, the distance between the light detection unit 14 and the compound semiconductor substrate 10, etc. so as to maximize the intensity of the light LT2 incident to the light detection unit 14.

The light LT2 consists of a component orthogonal to the surface 10a (hereinafter referred to as "orthogonal component Y") and a component parallel to the surface 10a (hereinafter referred to as "parallel component X"). The light detection unit 14 is able to detect the orthogonal component Y and parallel component X. Where the reflection coefficient of the orthogonal component Y is Rp and the reflection coefficient of the parallel component X is Rs, Eq (1) below holds. With this Eq (1) the amplitude ratio $\psi$ and phase difference $\Delta$ are obtained as measured data. In Eq (1), i indicates an imaginary number.

$$Rp/Rx = \tan(\psi)\exp(i\Delta) \quad (1)$$

The data of amplitude ratio $\psi$ and phase difference $\Delta$ is stored in a storage unit (not shown) such as a memory and a hard disk in the computer C connected to the light detection unit 14. If the wavelength of light LT1 is variable, data of amplitude ratio $\psi$ and phase difference $\Delta$ at each wavelength is obtained as measured data. When the wavelength of light LT1 is variable, the obtained data includes the number of measurement wavelengths times those in the case where the wavelength of light LT1 is fixed. Therefore, a single measurement enables measurement of optical properties of the compound semiconductor substrate 10, thicknesses of respective layers constituting the compound semiconductor substrate 10, and so on. The spectroscopic ellipsometry measurement also allows measurement of surface roughness of not more than 1 nm.

(Damage Evaluation Step)

The damage evaluation step S2 is to perform an analysis described below, using the measured data, to obtain spectra of optical constants (the real part $\in_1$ of the complex dielectric constant, the imaginary part $\in_2$ of the complex dielectric constant, the real part N of the complex index of refraction, and the imaginary part K of the complex index of refraction) of the compound semiconductor substrate 10.

For obtaining the spectra of the optical constants, a model structure of the compound semiconductor substrate 10 is first estimated. The model structure of the compound semiconductor substrate 10 has, for example, a compound semiconductor region 13, and a damage layer 11 provided on the compound semiconductor region 13. A layer 15 containing at least one of an oxide film and an uneven layer due to surface roughness, for example, may be formed on the damage layer 11. The layer 15 may also be an oxide film with an uneven surface. The layer 15 is preferably, for example, a layer in which an oxide and air are mixed. In the layer 15, for example, the oxide and air are mixed 50% by volume each, but the volume ratio of the oxide and air may be modified.

Next, an optical simulation is carried out with input of such parameters as thicknesses, refractive indices, extinction coefficients, etc. of the compound semiconductor region 13, damage layer 11, layer 15, etc. in the model structure, and fitting is performed between the result of the optical simulation and the measured data of the spectroscopic ellipsometry measurement. Furthermore, with feedback of the result of the fitting, another optical simulation is carried out again with reentry of the above parameters. This sequential operation is repeatedly carried out to determine the best model structure. The optical simulation and fitting are carried out well by use of optimum analysis software in the computer C.

Next, using the model structure determined as described above, the complex dielectric constant $\in$ and the complex index of refraction n are calculated from the measured data (data of amplitude ratio $\psi$ and phase difference $\Delta$ for each wavelength). Since there are a variety of known dielectric functions, it is preferable first to calculate the complex dielectric constant $\in$ and thereafter to calculate the complex index of refraction n. For example, the complex index of refraction n is calculated from the complex dielectric constant $\in$, using the dielectric function represented by Eq (2) below.

$$n = \sqrt{\in} \quad (2)$$

The complex dielectric constant $\in$ and the complex index of refraction n are represented by Eqs (3), (4) below. In Eq (3), $\in_1$ indicates the real part of the complex dielectric constant and $\in_2$ the imaginary part of the complex dielectric constant. In Eq (4) N indicates the real part of the complex index of refraction and K the imaginary part of the complex index of refraction.

$$\in = \in_1 + i\in_2 \quad (3)$$

$$n = N + iK \quad (4)$$

The spectra of the optical constants (the real part $\in_1$ of the complex dielectric constant, the imaginary part $\in_2$ of the complex dielectric constant, the real part N of the complex index of refraction, and the imaginary part K of the complex index of refraction) are obtained using the above Eqs (3), (4). The damage evaluation step S2 is to evaluate damage on the surface 10a of the compound semiconductor substrate 10, using a spectrum in a wavelength band containing a wavelength corresponding to the bandgap of the compound semiconductor substrate 10, in the spectra of the optical constants obtained by the spectroscopic ellipsometry measurement. Examples of such damage include damage, scratches, distortion, etc. due to polishing, etching, or the like.

In the damage evaluation method, execution of the foregoing spectroscopic ellipsometry measurement on the surface 10a of the compound semiconductor substrate 10 generates the exciton being a state of an electron and a hole coupled by Coulomb force. The exciton significantly affects, particularly, the spectra of the optical constants in the wavelength band containing the wavelength corresponding to the bandgap. Therefore, selective use of a part of the spectra of the optical constants can decrease the noise component, in comparison with the damage evaluation using the whole spectra of the optical constants obtained by the spectroscopic ellipsometry measurement. Therefore, it is feasible to achieve nondestructive and highly accurate evaluation on the level of damage on the surface 10a of the compound semiconductor substrate 10. Furthermore, the above damage evaluation method also enables simultaneous measurement of the thickness and optical properties of the damage layer 11, the thickness of the layer 15, the thickness of the oxide film, surface roughness, and so on.

It is noted that the tendency of influence of damage on the spectra of the optical constants is the same even if the model structure or the dielectric function used is different from the aforementioned model structure or dielectric function.

When the compound semiconductor substrate 10 is made, for example, of a monocrystalline material or polycrystalline material, the monocrystalline material or polycrystalline material turns into the amorphous form in a damaged region and thus it becomes easier to discriminate the damaged region from the other region without damage. For this reason, the damage becomes easier to detect and an improvement is made in the accuracy of damage evaluation.

The bandgap of the compound semiconductor substrate 10 is preferably not less than $1.6 \times 10^{-19}$ J (1 eV). In this case, the exciton is more likely to be generated by the spectroscopic ellipsometry measurement, so that the level of damage on the surface 10a of the compound semiconductor substrate 10 can be evaluated with higher accuracy. Particularly, where the compound semiconductor substrate 10 is made of a wide-gap semiconductor such as GaN, AlN, BN, ZnSe, or ZnO, the influence of exciton becomes stronger. On the other hand, even in cases where the compound semiconductor substrate 10 is made of a compound semiconductor with a small bandgap, the effect by exciton can be actualized by cooling approximately to the temperature of liquid nitrogen.

The compound semiconductor substrate 10 is preferably made of a nitride compound semiconductor containing at least one of B, Al, and Ga. Also, the compound semiconductor substrate 10 is preferably made of an oxide compound semiconductor containing at least one of Be and Zn. Furthermore, the compound semiconductor substrate 10 is preferably made of a ZnSe compound semiconductor. In each case, the bandgap of the compound semiconductor substrate 10 is increased, and thus the effect of exciton becomes easier to exhibit.

More specifically, the compound semiconductor substrate 10 is made, for example, of a III-V compound semiconductor such as GaAs or InP, a nitride compound semiconductor such as BN, GaN, AlN, or InN, a II-VI compound semiconductor such as ZnO or ZnS, an oxide compound semiconductor such as $Be_xO_y$, ZnO, $Ga_2O_3$, or $Al_2O_3$, a ZnSe compound semiconductor such as ZnSe, a ternary compound semiconductor such as GaAlN or InGaN, or a quaternary or higher compound semiconductor. These compound semiconductors may be doped with an impurity.

For example, in a case where the compound semiconductor substrate 10 is made of a gallium nitride compound semiconductor, the gallium nitride compound semiconductor suitably applicable is of the wurtzite structure or the zinc blende (cubic crystal) structure. In the case of the wurtzite structure, the surface 10a may be any one of the (0001) face called the C-plane, the (10-10) face called the M-plane, the (11-20) face called the A-plane, the (01-12) face called the R-plane, and the (10-11) face called the S-plane. The C-plane can be either a Ga plane consisting of Ga or an N plane consisting of N. Since the Ga plane is normally more resistant to etching, the surface 10a is preferably the Ga plane, but the surface 10a may be the N plane.

Figure 3:
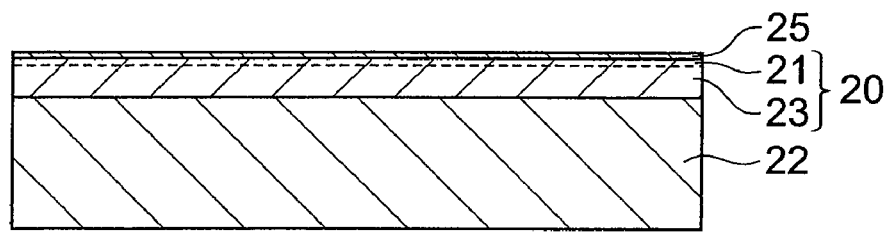
FIG. 3 is a sectional view schematically showing a compound semiconductor membrane provided on a substrate.

On the occasion of performing the spectroscopic ellipsometry measurement, a compound semiconductor membrane 20 (compound semiconductor member) shown in FIG. 3 may also be used instead of the compound semiconductor substrate 10.

FIG. 3 is a sectional view schematically showing a compound semiconductor membrane provided on a substrate. The substrate 22 shown in FIG. 3 is, for example, an amorphous substrate such as a glass substrate, or a monocrystalline substrate such as a sapphire substrate or Si substrate. From the viewpoint of eliminating influence of light reflected from the back surface of the substrate 22, the back surface of the substrate 22 is preferably provided with surface unevenness. However, if the analysis software is able to utilize a program that can take account of the influence of the light reflected from the back surface, the back surface may be a specular surface. The constituent material of the compound semiconductor membrane 20 may be the same as the compound semiconductor substrate 10. In this case, the spectroscopic ellipsometry measurement is carried out by projecting the light LT1 onto a surface 20a of the compound semiconductor membrane 20.

The model structure of the compound semiconductor membrane 20 has, for example, a compound semiconductor region 23, and a damage layer 21 provided on the compound semiconductor region 23. A layer 25 made of a constituent material similar to the layer 15 may be formed on the damage layer 21.

Method 1 to Method 16 of damage evaluation using the spectrum of the real part $\in_1$ of the complex dielectric constant, the spectrum of the imaginary part $\in_2$ of the complex dielectric constant, the spectrum of the real part N of the complex index of refraction, or the spectrum of the imaginary part K of the complex index of refraction will be described below in detail with reference to FIGS. 4A, 4B, 5A and 5B.

Figure 4A:
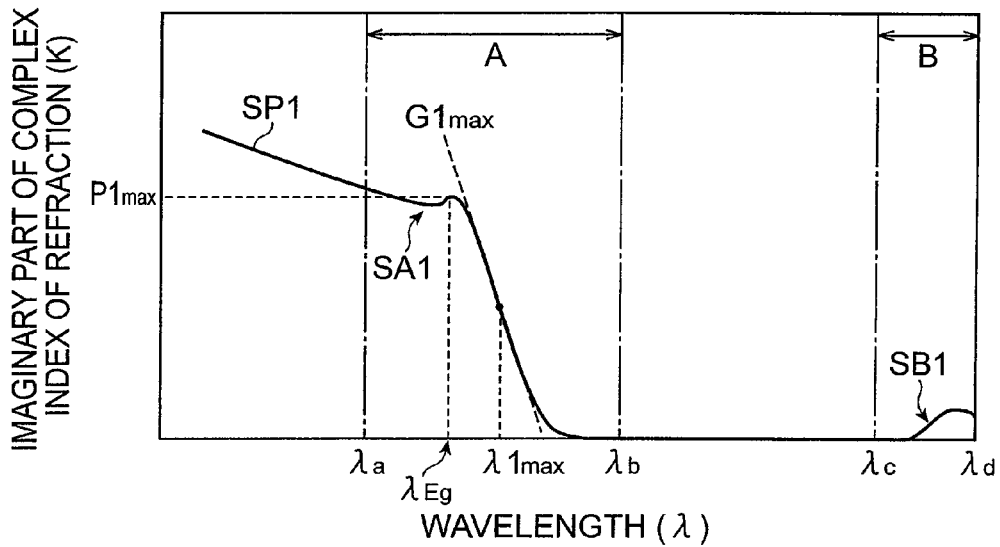
FIG. 4A is a graph schematically showing a spectrum SP1 of the imaginary part K of the complex index of refraction obtained by spectroscopic ellipsometry measurement.

FIG. 4A is a graph schematically showing the spectrum SP1 of the imaginary part K of the complex index of refraction obtained by spectroscopic ellipsometry measurement. The vertical axis of the graph represents the imaginary part K of the complex index of refraction, and the horizontal axis the wavelength λ. Energy or wave number may be taken on the horizontal axis. With reference to FIG. 4A, Method 1 to Method 4 will be described below in detail as methods of performing the damage evaluation using a spectrum SA1 in a wavelength band A from wavelength $\lambda_a$ to wavelength $\lambda_b$, in the spectrum SP1 of the imaginary part K of the complex index of refraction. The wavelength band A contains a wavelength $\lambda_{Eg}$ corresponding to the bandgap Eg of the compound semiconductor substrate 10. The wavelength $\lambda_a$ is preferably set, for example, to $(0.9 \times \lambda_{Eg})$ and the wavelength $\lambda_b$ is preferably set, for example, to $(1.1 \times \lambda_{Eg})$.

<Method 1>

Method 1 is to evaluate damage on the surface 10a of the compound semiconductor substrate 10, using a maximum absolute value $G1_{max}$ of the slope of the spectrum SA1 in the wavelength band A. The maximum $G1_{max}$ is the same value as an absolute value of an extremum of the first derivative of the spectrum SA1. The maximum $G1_{max}$ tends to decrease with increasing level of damage. Therefore, the use of the maximum $G1_{max}$ in the damage evaluation enables the level of damage to be quantified.

Method 1 is suitably applicable to production of the compound semiconductor substrate 10. The compound semiconductor substrate is determined to be nondefective when the maximum $G1_{max}$ is not less than a predetermined threshold, whereby the compound semiconductor substrate 10 with a low level of damage can be produced at a high yield.

<Method 2>

Method 2 is to evaluate damage on the surface 10a of the compound semiconductor substrate 10, using a wavelength $\lambda1_{max}$ at which the absolute value of the slope of the spectrum SA1 in the wavelength band A is maximum $G1_{max}$. The wavelength $\lambda1_{max}$ tends to decrease with increasing level of damage. Therefore, the use of the wavelength $\lambda1_{max}$ in the damage evaluation enables the level of damage to be quantified.

Method 2 is suitably applicable to production of the compound semiconductor substrate 10. The compound semiconductor substrate is determined to be nondefective when the wavelength $\lambda1_{max}$ is not less than a predetermined threshold, whereby the compound semiconductor substrate 10 with a low level of damage can be produced at a high yield.

<Method 3>

Method 3 is to evaluate damage on the surface 10a of the compound semiconductor substrate 10, using a maximum $P1_{max}$ of the spectrum SA1 in the wavelength band A. The maximum $P1_{max}$ tends to decrease with increasing level of damage. Therefore, the use of the maximum $P1_{max}$ in the damage evaluation enables the level of damage to be quantified.

Method 3 is suitably applicable to production of the compound semiconductor substrate 10. The compound semiconductor substrate is determined to be nondefective when the maximum $P1_{max}$ is not less than a predetermined threshold, whereby the compound semiconductor substrate 10 with a low level of damage can be produced at a high yield.

<Method 4>

Method 4 uses a peak SB1 in another wavelength band B located on the longer wavelength side than the wavelength band A. The wavelength band B is a wavelength band from wavelength $\lambda_c$ larger than the wavelength $\lambda_b$ to wavelength $\lambda_d$. The peak SB1 appears in the spectrum SP1 of the imaginary part K of the complex index of refraction when light is reflected at least once (e.g., with multiple reflection) between the compound semiconductor region 13 and the damage layer 11. The peak SB1 is observed when the level of damage is high. The use of this peak SB1 enables the level of damage on the surface 10a to be evaluated with high accuracy.

The compound semiconductor substrate 10 is preferably one of substrate A1 to substrate A3 described below. In each case, a gallium nitride compound semiconductor substrate is obtained with a low level of damage on its surface. Where the compound semiconductor substrate 10 is made, for example, of a gallium nitride compound semiconductor, the wavelength $\lambda_{Eg}$ is about 365 nm.

(Substrate A1) Gallium nitride compound semiconductor substrate in which the absolute value of the difference between the imaginary part K of the complex index of refraction at 360 nm and the imaginary part K of the complex index of refraction at 370 nm is not less than 0.045.

(Substrate A2) Gallium nitride compound semiconductor substrate in which the absolute value of the imaginary part K of the complex index of refraction at 370 nm is not more than 0.18.

(Substrate A3) Gallium nitride compound semiconductor substrate in which the wavelength $\lambda 1_{max}$ at which the absolute value of the slope of the spectrum SA1 in the wavelength band A is maximum is not less than 350 nm, where the wavelength $\lambda_a$ is 300 nm and the wavelength $\lambda_b$ 400 nm.

Figure 4B:
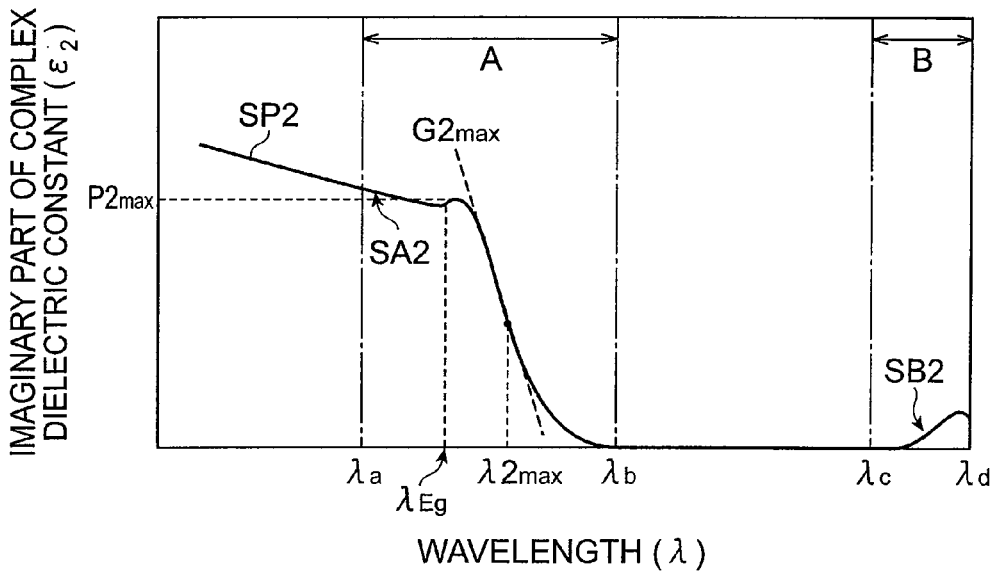
FIG. 4B is a graph schematically showing a spectrum SP2 of the imaginary part $\in_2$, of the complex dielectric constant obtained by spectroscopic ellipsometry measurement.

FIG. 4B is a graph schematically showing the spectrum SP2 of the imaginary part $\in_2$ of the complex dielectric constant obtained by spectroscopic ellipsometry measurement. The vertical axis of the graph represents the imaginary part $\in_2$ of the complex dielectric constant, and the horizontal axis the wavelength $\lambda$. Energy or wave number may be taken on the horizontal axis. With reference to FIG. 4B, Method 5 to Method 8 will be described in detail as methods of performing damage evaluation using a spectrum SA2 in the wavelength band A in the spectrum SP2 of the imaginary part $£_2$ of the complex dielectric constant.

<Method 5>

Method 5 is to evaluate damage on the surface 10a of the compound semiconductor substrate 10, using a maximum absolute value $G2_{max}$ of the slope of the spectrum SA2 in the wavelength band A. The maximum $G2_{max}$ is the same value as an absolute value of an extremum of the first derivative of the spectrum SA2. The maximum $G2_{max}$ tends to decrease with increasing level of damage. Therefore, the use of the maximum $G2_{max}$ in the damage evaluation enables the level of damage to be quantified.

Method 5 is suitably applicable to production of the compound semiconductor substrate 10. The compound semiconductor substrate is determined to be nondefective when the maximum $G2_{max}$ is not less than a predetermined threshold, whereby the compound semiconductor substrate 10 with a low level of damage can be produced at a high yield.

<Method 6>

Method 6 is to evaluate damage on the surface 10a of the compound semiconductor substrate 10, using a wavelength $\lambda 2_{max}$ at which the absolute value of the slope of the spectrum SA2 in the wavelength band A is maximum $G2_{max}$. The wavelength $\lambda 2_{max}$ tends to decrease with increasing level of damage. Therefore, the use of the wavelength $\lambda 2_{max}$ in the damage evaluation enables the level of damage to be quantified.

Method 6 is suitably applicable to production of the compound semiconductor substrate 10. The compound semiconductor substrate is determined to be nondefective when the wavelength $\lambda 2_{max}$ is not less than a predetermined threshold, whereby the compound semiconductor substrate 10 with a low level of damage can be produced at a high yield.

<Method 7>

Method 7 is to evaluate damage on the surface 10a of the compound semiconductor substrate 10, using a maximum $P2_{max}$ of the spectrum SA2 in the wavelength band A. The maximum $P2_{max}$ tends to decrease with increasing level of damage. Therefore, the use of the maximum $P2_{max}$ in the damage evaluation enables the level of damage to be quantified.

Method 7 is suitably applicable to production of the compound semiconductor substrate 10. The compound semiconductor substrate is determined to be nondefective when the maximum $P2_{max}$ is not less than a predetermined threshold, whereby the compound semiconductor substrate 10 with a low level of damage can be produced at a high yield.

<Method 8>

Method 8 uses a peak SB2 in another wavelength band B located on the longer wavelength side than the wavelength band A. The peak SB2 appears in the spectrum SP2 of the imaginary part $\in_2$ of the complex dielectric constant when light is reflected at least once (e.g., with multiple reflection) between the compound semiconductor region 13 and the damage layer 11. The peak SB2 is observed when the level of damage is high. The use of this peak SB2 enables the level of damage on the surface 10a to be evaluated with high accuracy.

The compound semiconductor substrate 10 is preferably one of substrate A4 to substrate A6 described below. In each case, a gallium nitride compound semiconductor substrate is obtained with a low level of damage on its surface.

(Substrate A4) Gallium nitride compound semiconductor substrate in which the absolute value of the difference between the imaginary part $\in_2$ of the complex dielectric constant at 360 nm and the imaginary part $\in_2$ of the complex dielectric constant at 370 nm is not less than 0.24.

(Substrate A5) Gallium nitride compound semiconductor substrate in which the absolute value of the imaginary part $\in_2$ of the complex dielectric constant at 370 nm is not more than 0.9.

(Substrate A6) Gallium nitride compound semiconductor substrate in which the wavelength $\lambda 2_{max}$ at which the absolute value of the slope of the spectrum SA2 in the wavelength band A is maximum is not less than 350 nm, where the wavelength $\lambda_a$ is 300 nm and the wavelength $\lambda_b$ 400 nm.

Figure 5A:
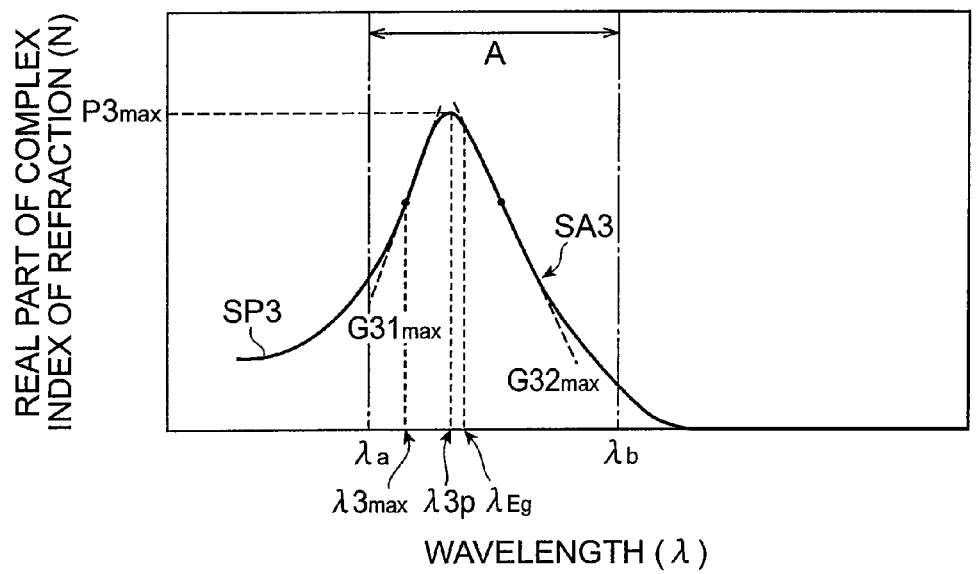
FIG. 5A is a graph schematically showing a spectrum SP3 of the real part N of the complex index of refraction obtained by spectroscopic ellipsometry measurement.

FIG. 5A is a graph schematically showing a spectrum SP3 of the real part N of the complex index of refraction obtained by spectroscopic ellipsometry measurement. The vertical axis of the graph represents the real part N of the complex index of refraction, and the horizontal axis the wavelength $\lambda$. Energy or wave number may be taken on the horizontal axis.

With reference to FIG. 5A, Method 9 to Method 12 will be described in detail as methods of performing damage evaluation using a spectrum SA3 in the wavelength band A in the spectrum SP3 of the real part N of the complex index of refraction.

<Method 9>

Method 9 is to evaluate damage on the surface $10a$ of the compound semiconductor substrate 10, using a maximum absolute value $G31_{max}$ of the slope in a portion ($\lambda_a$ to $\lambda3_p$) located on the shorter wavelength side than the wavelength $\lambda3_p$ corresponding to a maximum $P3_{max}$ in the spectrum SA3 in the wavelength band A. The maximum $G31_{max}$ tends to decrease with increasing level of damage. Therefore, the use of the maximum $G31_{max}$ in the damage evaluation enables the level of damage to be quantified.

Method 9 is suitably applicable to production of the compound semiconductor substrate 10. The compound semiconductor substrate is determined to be nondefective when the maximum $G31_{max}$ is not less than a predetermined threshold, whereby the compound semiconductor substrate 10 with a low level of damage can be produced at a high yield.

<Method 10>

Method 10 is to evaluate damage on the surface $10a$ of the compound semiconductor substrate 10, using a maximum absolute value $G32_{max}$ of the slope in a portion ($\lambda3_p$ to $\lambda_b$) located on the longer wavelength side than the wavelength $\lambda3_p$ corresponding to the maximum $P3_{max}$ in the spectrum SA3 in the wavelength band A. The maximum $G32_{max}$ tends to decrease with increasing level of damage. Therefore, the use of the maximum $G32_{max}$ in the damage evaluation enables the level of damage to be quantified.

Method 10 is suitably applicable to production of the compound semiconductor substrate 10. The compound semiconductor substrate is determined to be nondefective when the maximum $G32_{max}$ is not less than a predetermined threshold, whereby the compound semiconductor substrate 10 with a low level of damage can be produced at a high yield.

<Method 11>

Method 11 is to evaluate damage on the surface $10a$ of the compound semiconductor substrate 10, using a wavelength $\lambda3_{max}$ at which the absolute value of the slope in the portion ($\lambda_a$ to $\lambda3_p$) located on the shorter wavelength side than the wavelength $\lambda3_p$ corresponding to the maximum $P3_{max}$ in the spectrum SA3 in the wavelength band A is maximum $G31_{max}$. The wavelength $\lambda3_{max}$ tends to decrease with increasing level of damage. Therefore, the use of the wavelength $\lambda3_{max}$ in the damage evaluation enables the level of damage to be quantified.

Method 11 is suitably applicable to production of the compound semiconductor substrate 10. The compound semiconductor substrate is determined to be nondefective when the wavelength $\lambda3_{max}$ is not less than a predetermined threshold, whereby the compound semiconductor substrate 10 with a low level of damage can be produced at a high yield.

<Method 12>

Method 12 is to evaluate damage on the surface $10a$ of the compound semiconductor substrate 10, using the maximum $P3_{max}$ of the spectrum SA3 in the wavelength band A. The maximum $P3_{max}$ tends to decrease with increasing level of damage. Therefore, the use of the maximum $P3_{max}$ in the damage evaluation enables the level of damage to be quantified.

Method 12 is suitably applicable to production of the compound semiconductor substrate 10. The compound semiconductor substrate is determined to be nondefective when the maximum $P3_{max}$ is not less than a predetermined threshold, whereby the compound semiconductor substrate 10 with a low level of damage can be produced at a high yield.

The compound semiconductor substrate 10 is preferably substrate A7 or substrate A8 described below. In either case, a gallium nitride compound semiconductor substrate is obtained with a low level of damage on its surface.

(Substrate A7) Gallium nitride compound semiconductor substrate in which the absolute value of the difference between the real part N of the complex index of refraction at 365 nm and the real part N of the complex index of refraction at 375 nm is not less than 0.035.

(Substrate A8) Gallium nitride compound semiconductor substrate in which the maximum $P3_{max}$ of the spectrum SA3 in the wavelength band A is not less than 2.7, where the wavelength $\lambda_a$ is 300 nm and the wavelength 400 nm.

Figure 5B:
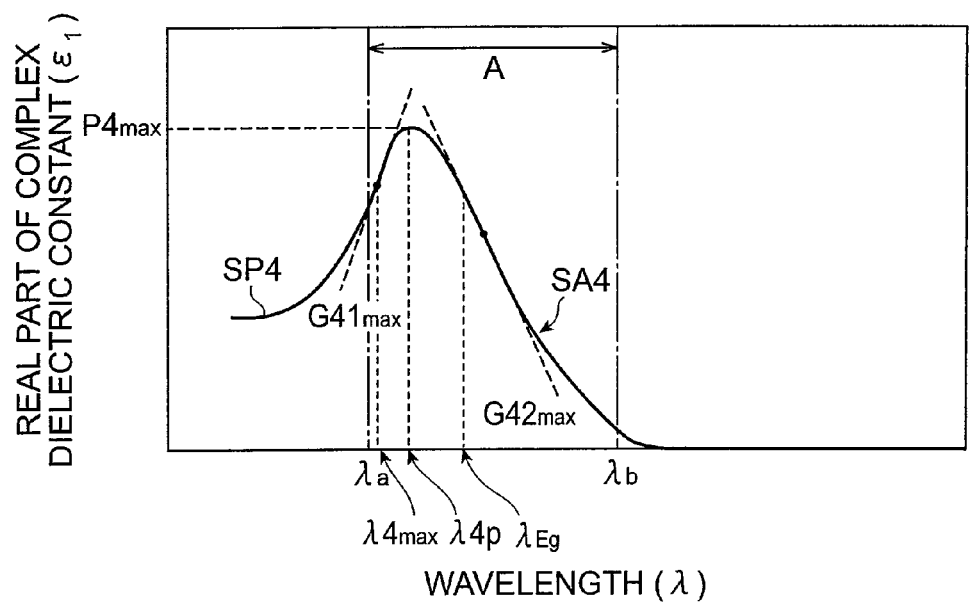
FIG. 5B is a graph schematically showing a spectrum SP4 of the real part $\in_1$ of the complex dielectric constant obtained by spectroscopic ellipsometry measurement.

FIG. 5B is a graph schematically showing a spectrum SP4 of the real part $\in_1$ of the complex dielectric constant obtained by spectroscopic ellipsometry measurement. The vertical axis of the graph represents the real part $\in_1$ of the complex dielectric constant, and the horizontal axis the wavelength $\lambda$. Energy or wave number may be taken on the horizontal axis. With reference to FIG. 5B, Method 13 to Method 16 will be described in detail as methods of performing damage evaluation using a spectrum SA4 in the wavelength band A in the spectrum SP4 of the real part $\in_1$ of the complex dielectric constant.

<Method 13>

Method 13 is to evaluate damage on the surface $10a$ of the compound semiconductor substrate 10, using a maximum absolute value $G41_{max}$ of the slope in a portion ($\lambda_a$ to $\lambda4_p$) located on the shorter wavelength side than a wavelength $\lambda4_p$ corresponding to a maximum $P4_{max}$ in the spectrum SA4 in the wavelength band A. The maximum $G41_{max}$ tends to decrease with increasing level of damage. Therefore, the use of the maximum $G41_{max}$ in the damage evaluation enables the level of damage to be quantified.

Method 13 is suitably applicable to production of the compound semiconductor substrate 10. The compound semiconductor substrate is determined to be nondefective when the maximum $G41_{max}$ is not less than a predetermined threshold, whereby the compound semiconductor substrate 10 with a low level of damage can be produced at a high yield.

<Method 14>

Method 14 is to evaluate damage on the surface $10a$ of the compound semiconductor substrate 10, using a maximum absolute value $G42_{max}$ of the slope in a portion ($\lambda4_p$ to $\lambda_b$) located on the longer wavelength side than the wavelength $\lambda4_p$ corresponding to the maximum $P4_{max}$ in the spectrum SA4 in the wavelength band A. The maximum $G42_{max}$ tends to decrease with increasing level of damage. Therefore, the use of the maximum $G42_{max}$ in the damage evaluation enables the level of damage to be quantified.

Method 14 is suitably applicable to production of the compound semiconductor substrate 10. The compound semiconductor substrate is determined to be nondefective when the maximum $G42_{max}$ is not less than a predetermined threshold, whereby the compound semiconductor substrate 10 with a low level of damage can be produced at a high yield.

<Method 15>

Method 15 is to evaluate damage on the surface $10a$ of the compound semiconductor substrate 10, using a wavelength $\lambda4_{max}$ at which the absolute value of the slope in the portion ($\lambda_a$ to $\lambda4_p$) located on the shorter wavelength side than the wavelength $\lambda4_p$ corresponding to the maximum $P4_{max}$ in the spectrum SA4 in the wavelength band A is maximum $G41_{max}$. The wavelength $\lambda4_{max}$ tends to decrease with increasing level of damage. Therefore, the use of the wavelength $\lambda 4_{max}$ in the damage evaluation enables the level of damage to be quantified.

Method 15 is suitably applicable to production of the compound semiconductor substrate 10. The compound semiconductor substrate is determined to be nondefective when the wavelength $\lambda 4_{max}$ is not less than a predetermined threshold, whereby the compound semiconductor substrate 10 with a low level of damage can be produced at a high yield.

<Method 16>

Method 16 is to evaluate damage on the surface 10a of the compound semiconductor substrate 10, using the maximum $P4_{max}$ of the spectrum SA4 in the wavelength band A. The maximum $P4_{max}$ tends to decrease with increasing level of damage. Therefore, the use of the maximum $P4_{max}$ in the damage evaluation enables the level of damage to be quantified.

Method 16 is suitably applicable to production of the compound semiconductor substrate 10. The compound semiconductor substrate is determined to be nondefective when the maximum $P4_{max}$ is not less than a predetermined threshold, whereby the compound semiconductor substrate 10 with a low level of damage can be produced at a high yield.

The compound semiconductor substrate 10 is preferably substrate A9 or substrate A10 described below. In either case, a gallium nitride compound semiconductor substrate is obtained with a low level of damage on its surface.

(Substrate A9) Gallium nitride compound semiconductor substrate in which the absolute value of the difference between the real part $\in_1$ of the complex dielectric constant at 365 nm and the real part $\in_1$ of the complex dielectric constant at 375 nm is not less than 0.13.

(Substrate A10) Gallium nitride compound semiconductor substrate in which the maximum $P4_{max}$ of the spectrum SA4 in the wavelength band A is not less than 7.2, where the wavelength $\lambda_a$ is 300 nm and the wavelength $\lambda_b$ 400 nm.

The compound semiconductor substrate 10 is preferably substrate A11. In this case, a gallium nitride compound semiconductor substrate is obtained with a low level of damage on its surface.

(Substrate A11) Gallium nitride compound semiconductor substrate the thickness of the layer 15 formed on the surface 10a of which is not more than 6 nm.

Damage may also be evaluated for the compound semiconductor membrane 20 shown in FIG. 3, instead of the compound semiconductor substrate 10. In this case, use of Method 1 to Method 16 permits the level of damage on the surface 20a of the compound semiconductor membrane 20 provided on the substrate 22 to be evaluated with high accuracy and permits the level of damage to be quantified. Since the influence of damage on the compound semiconductor membrane 20 becomes relatively large, the damage becomes easier to detect even if the level of damage is low.

Furthermore, use of Method 1 to Method 16 permits the compound semiconductor membrane 20 with a low level of damage to be produced at a high yield.

The compound semiconductor membrane 20 is preferably one of membrane B1 to membrane B11 described below. In each case, a gallium nitride compound semiconductor membrane is obtained with a low level of damage on its surface. Where the compound semiconductor membrane 20 is made, for example, of a gallium nitride compound semiconductor, the wavelength $\lambda_{Eg}$ is about 365 nm.

(Membrane B1) Gallium nitride compound semiconductor membrane in which the absolute value of the difference between the imaginary part K of the complex index of refraction at 360 nm and the imaginary part K of the complex index of refraction at 370 nm is not less than 0.045.

(Membrane B2) Gallium nitride compound semiconductor membrane in which the absolute value of the imaginary part K of the complex index of refraction at 370 nm is not more than 0.18.

(Membrane B3) Gallium nitride compound semiconductor membrane in which the wavelength $\lambda 1_{max}$ at which the absolute value of the slope of the spectrum SA1 in the wavelength band A is maximum is not less than 350 nm, where the wavelength $\lambda_a$ is 300 nm and the wavelength $\lambda_b$ 400 nm.

(Membrane B4) Gallium nitride compound semiconductor membrane in which the absolute value of the difference between the imaginary part $\in_2$ of the complex dielectric constant at 360 nm and the imaginary part $\in_2$ of the complex dielectric constant at 370 nm is not less than 0.24.

(Membrane B5) Gallium nitride compound semiconductor membrane in which the absolute value of the imaginary part $\in_2$ of the complex dielectric constant at 370 nm is not more than 0.9.

(Membrane B6) Gallium nitride compound semiconductor membrane in which the wavelength $\lambda 2_{max}$ at which the absolute value of the slope of the spectrum SA2 in the wavelength band A is maximum is not less than 350 nm, where the wavelength $\lambda_a$ is 300 nm and the wavelength $\lambda_b$ 400 nm.

(Membrane B7) Gallium nitride compound semiconductor membrane in which the absolute value of the difference between the real part N of the complex index of refraction at 365 nm and the real part N of the complex index of refraction at 375 nm is not less than 0.035.

(Membrane B8) Gallium nitride compound semiconductor membrane in which the maximum $P3_{max}$ of the spectrum SA3 in the wavelength band A is not less than 2.7, where the wavelength $\lambda_a$ is 300 nm and the wavelength $\lambda_b$ 400 nm.

(Membrane B9) Gallium nitride compound semiconductor membrane in which the absolute value of the difference between the real part $\in_1$ of the complex dielectric constant at 365 nm and the real part $\in_1$ of the complex dielectric constant at 375 nm is not less than 0.13.

(Membrane B10) Gallium nitride compound semiconductor membrane in which the maximum $P4_{max}$ of the spectrum SA4 in the wavelength band A is not less than 7.2, where the wavelength $\lambda_a$ is 300 nm and the wavelength $\lambda_b$ 400 nm.

(Membrane B11) Gallium nitride compound semiconductor membrane the thickness of the layer 25 formed on the surface 20a of which is not more than 6 nm.

(Thin Film Forming Step)

Figure 6A:
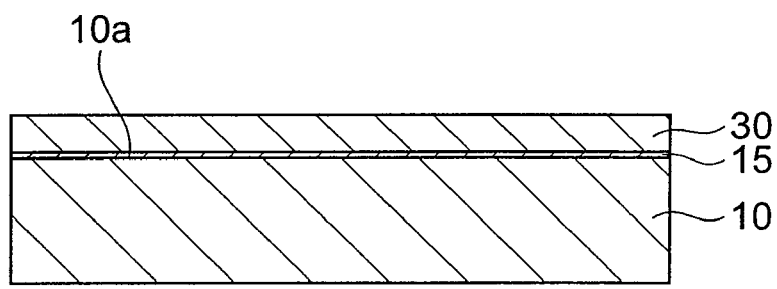
FIG. 6A is a sectional view schematically showing a compound semiconductor substrate in a thin film forming step.
Figure 6B:
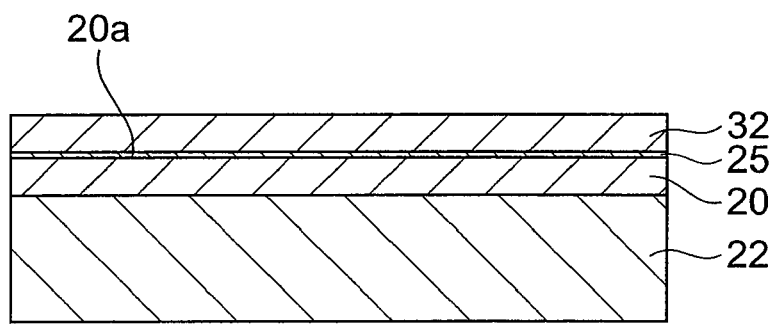
FIG. 6B is a sectional view schematically showing a compound semiconductor membrane in the thin film forming step.

FIG. 6A is a sectional view schematically showing a compound semiconductor substrate in the thin film forming step. FIG. 6B is a sectional view schematically showing a compound semiconductor membrane in the thin film forming step. The thin film forming step S3 is preferably carried out after the damage evaluation step S2.

The thin film forming step S3 is to form a thin film 30 on the surface 10a of the compound semiconductor substrate 10, as shown in FIG. 6A. The thin film 30 is formed, for example, by an epitaxial growth method. The thin film 30 is, for example, a compound semiconductor film, an oxide film, a ZnO film, an amorphous film, or the like. As the thin film 30 is formed on the surface 10a of the compound semiconductor substrate 10 with a low level of damage, an improvement is made in crystallinity and in surface roughness of the thin film 30. A layer 15 may be interposed between the surface 10a of the compound semiconductor substrate 10 and the thin film 30.

The thin film 30 is preferably a gallium nitride compound semiconductor membrane formed on any one of the aforementioned substrate A1 to substrate A11. Since this gallium nitride compound semiconductor membrane is formed on one of substrate A1 to substrate A11 with a low level of damage on the surface, an improvement is made in crystallinity and in surface roughness.

In the thin film forming step S3, as shown in FIG. 6B, a thin film 32 may be formed on a surface 20a of compound semiconductor membrane 20. The thin film 32 is formed, for example, by an epitaxial growth method. The thin film 32 can be a film similar to the thin film 30. As the thin film 32 is formed on the surface 20a of the compound semiconductor membrane 20 with a low level of damage, an improvement is made in crystallinity and surface roughness of the thin film 32. A layer 25 may be interposed between the surface 20a of the compound semiconductor membrane 20 and the thin film 32.

The thin film 32 is preferably a gallium nitride compound semiconductor membrane formed on any one of the aforementioned membrane B1 to membrane B11. Since this gallium nitride compound semiconductor membrane is formed on one of membrane B1 to membrane B11 with a low level of damage on the surface, an improvement is made in crystallinity and in surface roughness.

(Electrode Forming Step)

Figure 7A:
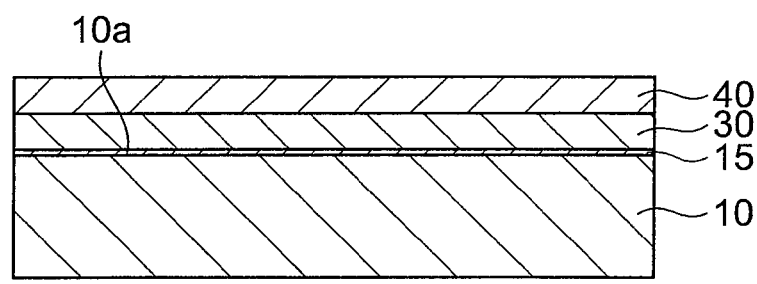
FIG. 7A is a sectional view schematically showing a compound semiconductor substrate in an electrode forming step.
Figure 7B:
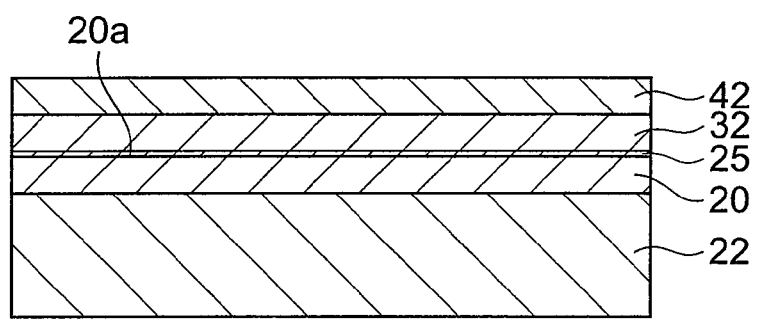
FIG. 7B is a sectional view schematically showing a compound semiconductor membrane in the electrode forming step.

FIG. 7A is a sectional view schematically showing a compound semiconductor substrate in the electrode forming step. FIG. 7B is a sectional view schematically showing a compound semiconductor membrane in the electrode forming step. The electrode forming step S4 is preferably carried out after the damage evaluation step S2 and more preferably carried out after the thin film forming step S3.

The electrode forming step S4 is to form an electrode 40, for example, of a metal film or the like on the thin film 30, as shown in FIG. 7A. In this case, the thin film 30 has excellent crystallinity and reduced surface roughness, and occurrence of damage can be suppressed at the interface between the thin film 30 and the electrode 40.

The electrode 40 may also be formed directly on the surface 10a of the compound semiconductor substrate 10. In that case, when the compound semiconductor substrate 10 with a low level of damage is used, occurrence of damage can be suppressed at the interface between the compound semiconductor substrate 10 and the electrode 40.

The electrode forming step S4 may also be to form an electrode 42 on the thin film 32, as shown in FIG. 7B. In this case, the thin film 32 has excellent crystallinity and reduced surface roughness, and occurrence of damage can be suppressed at the interface between the thin film 32 and the electrode 42.

The electrode 40 may also be formed directly on the surface 20a of the compound semiconductor membrane 20. In that case, when the compound semiconductor membrane 20 with a low level of damage is used, occurrence of damage can be suppressed at the interface between the compound semiconductor membrane 20 and the electrode 42.

A compound semiconductor device can be produced through the steps described above.

The preferred embodiments of the present invention were described above in detail, but it is noted that the present invention is not limited to the above embodiments.

Subsequently, Experiment Examples associated with the above embodiments will be described.

Experiment Example 1

First, a monocrystalline GaN ingot was sliced to prepare a monocrystalline GaN substrate with the diameter of 2 inches. The surface of the monocrystalline GaN substrate prepared was polished and thereafter the surface was dry-etched by reactive ion etching (RIE). The conditions for dry etching were as follows.

Etching gas: Ar gas
Supplied power: 200 W
Pressure in chamber: 1.3 Pa (10 mTorr)
Etching time: 10 minutes Thereafter, in order to eliminate damage from the surface, the monocrystalline GaN substrate was immersed in a 5% $NH_4OH$ solution at 40° C. for 15 minutes to effect wet etching. The monocrystalline GaN substrate of Experiment Example 1 was obtained as described above.

Experiment Example 2

First, a monocrystalline GaN ingot was sliced to prepare a monocrystalline GaN substrate with the diameter of 2 inches. The surface of the monocrystalline GaN substrate prepared was roughly polished and thereafter the surface was further polished by means of diamond abrasive grains with the grain size of 0.5 µm. Thereafter, the surface was cleaned with isopropyl alcohol. The monocrystalline GaN substrate of Experiment Example 2 was obtained as described above.

Experiment Example 3

A monocrystalline GaN substrate of Experiment Example 3 was obtained in the same manner as in Experiment Example 2 except that diamond abrasive grains with the grain size of 0.1 µm were used instead of the diamond abrasive grains with the grain size of 0.5 µm.

Experiment Example 4

A monocrystalline GaN substrate of Experiment Example 4 was obtained by effecting dry etching in Experiment Example 1 on a monocrystalline GaN substrate obtained in the same manner as in Experiment Example 3.

Experiment Example 5

A monocrystalline GaN substrate of Experiment Example 5 was obtained by effecting wet etching with a diluted $H_3PO_4$ solution on a monocrystalline GaN substrate obtained in the same manner as in Experiment Example 3.

(Photoluminescence Measurement and Fluorescence Microscope Measurement)

Photoluminescence measurement was carried out for each of the surfaces of the monocrystalline GaN substrates of Experiment Example 1 to Experiment Example 5. In the photoluminescence measurement a He—Cd laser capable of emitting a laser beam with the wavelength of 325 nm was used as a light source. The laser beam was made incident normally to the surface of each monocrystalline GaN substrate to obtain an emission spectrum. In each emission spectrum a peak was observed near 365 nm.

The photoluminescence measurement was carried out at wavelength intervals of 0.5 nm and values near the peak were interpolated by a normal distribution. The background was adjusted by linear approximation of wing portions of the peak.

Fluorescence microscope measurement was carried out for each of the surfaces of the monocrystalline GaN substrates of Experiment Example 1 to Experiment Example 5. The fluorescence microscope measurement was carried out using an optical system capable of transmitting light of wavelengths of not less than 345 nm.

It was found from the results of the photoluminescence measurement and the fluorescence microscope measurement that there was a correlation between photoluminescence intensities (PL intensities) in the photoluminescence measurement and fluorescence intensities in the fluorescence microscope measurement.

Figure 8:
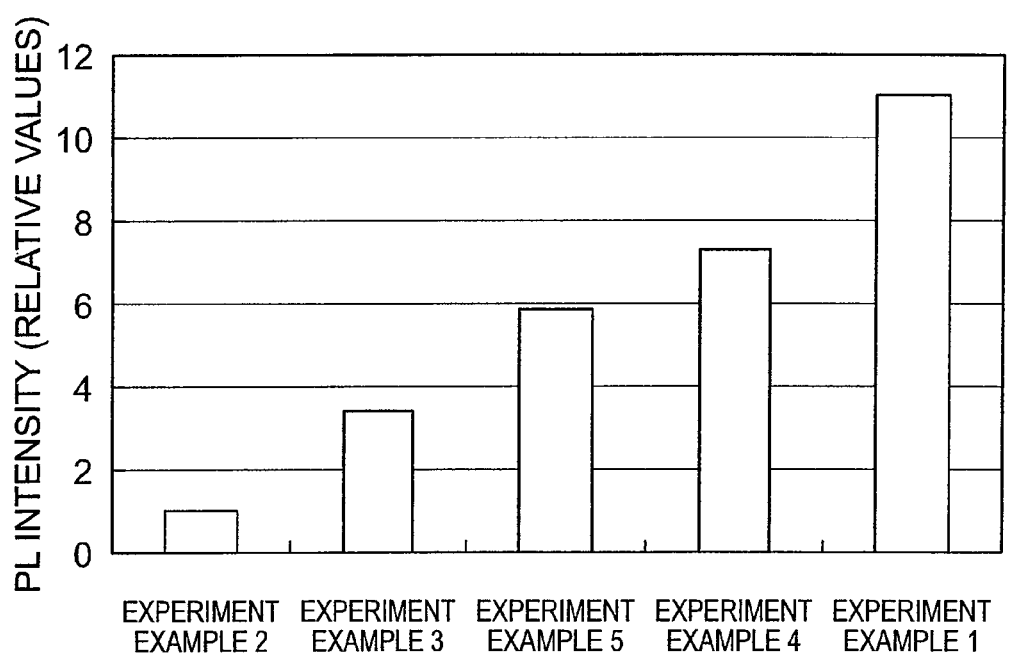
FIG. 8 shows PL intensities of a peak near 365 nm in respective emission spectra obtained by photoluminescence measurement on surfaces of monocrystalline GaN substrates of Experiment Example 1 to Experiment Example 5.

FIG. 8 shows the PL intensities of the peak near 365 nm in the respective emission spectra obtained by the photoluminescence measurement on the surfaces of the monocrystalline GaN substrates of Experiment Example 1 to Experiment Example 5. The values of PL intensities are relative values with respect to 1 for the PL intensity of Experiment Example 2. FIG. 8 shows that the PL intensity decreases and the level of damage on the surface increases, in the order of Experiment Example 1, Experiment Example 4, Experiment Example 5, Experiment Example 3, and Experiment Example 2.

(Spectroscopic Ellipsometry Measurement)

The spectroscopic ellipsometry measurement was carried out for the surfaces of the monocrystalline GaN substrates of Experiment Example 1 to Experiment Example 5. The spectroscopic ellipsometer 16 used was the spectroscopic ellipsometer available from SOPRA Co. The spectroscopic ellipsometry measurement was conducted at angles of incidence of the light LT1, 65°, 70°, and 75°.

(Damage Evaluation)

The model structure of the monocrystalline GaN substrate was a monocrystalline GaN substrate with a damage layer as a surface layer. Furthermore, it was assumed that there was a mixed layer of an oxide film and an uneven layer on the damage layer. The mixed layer was assumed to be a mixture of oxide and air 50% each by use of effective medium approximation. The optical simulation and fitting were conducted using this model structure. These resulted in obtaining the spectrum of the real part $\in_1$ of the complex dielectric constant, the spectrum of the imaginary part $\in_2$ of the complex dielectric constant, the spectrum of the real part N of the complex index of refraction, and the spectrum of the imaginary part K of the complex index of refraction.

Figure 9:
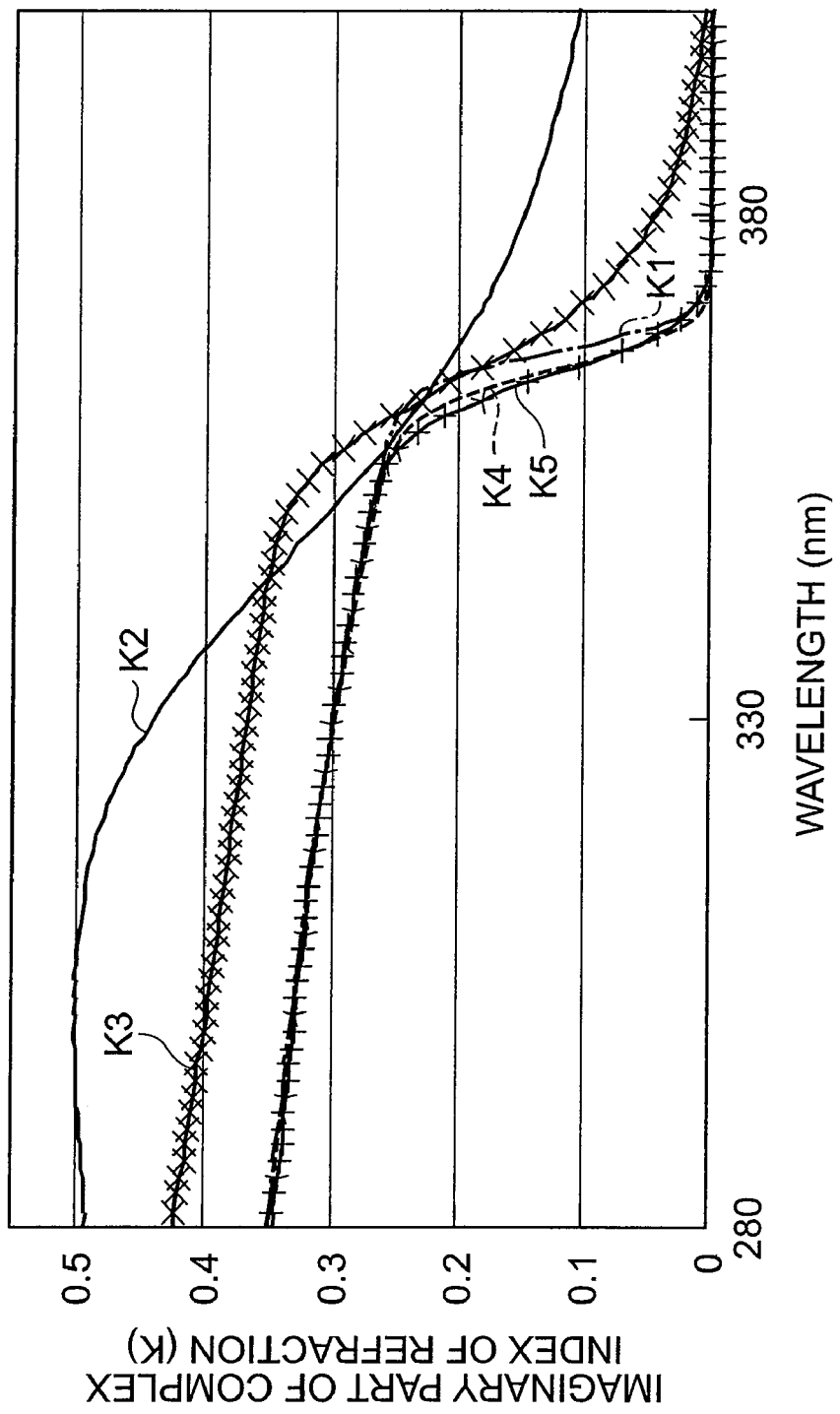
FIG. 9 is a graph showing part of spectra of the imaginary part K of the complex index of refraction obtained by spectroscopic ellipsometry measurement.

FIG. 9 is a graph showing part of spectra of the imaginary part K of the complex index of refraction obtained by the spectroscopic ellipsometry measurement. Spectra K1 to K5 in the graph indicate spectra in the wavelength range of 280 to 400 nm of the imaginary part K of the complex index of refraction of the monocrystalline GaN substrates of Experiment Example 1 to Experiment Example 5, respectively. It was found from the graph that the spectra K1 to K5 had a spread on the longer wavelength side and on the shorter wavelength side than 365 nm. It was also found that values of the imaginary part K of the complex index of refraction on the longer wavelength side and on the shorter wavelength side than 365 nm tended to increase with increasing level of damage.

In the spectra K1 to K5, absolute values of the difference between the imaginary part K of the complex index of refraction at 360 nm and the imaginary part K of the complex index of refraction at 370 nm were 0.215, 0.044, 0.138, 0.200, and 0.188, respectively. In the spectra K1 to K5, absolute values of the imaginary part K of the complex index of refraction at 370 nm were 0.012, 0.023, 0.031, 0.118, and 0.187, respectively.

Figure 10:
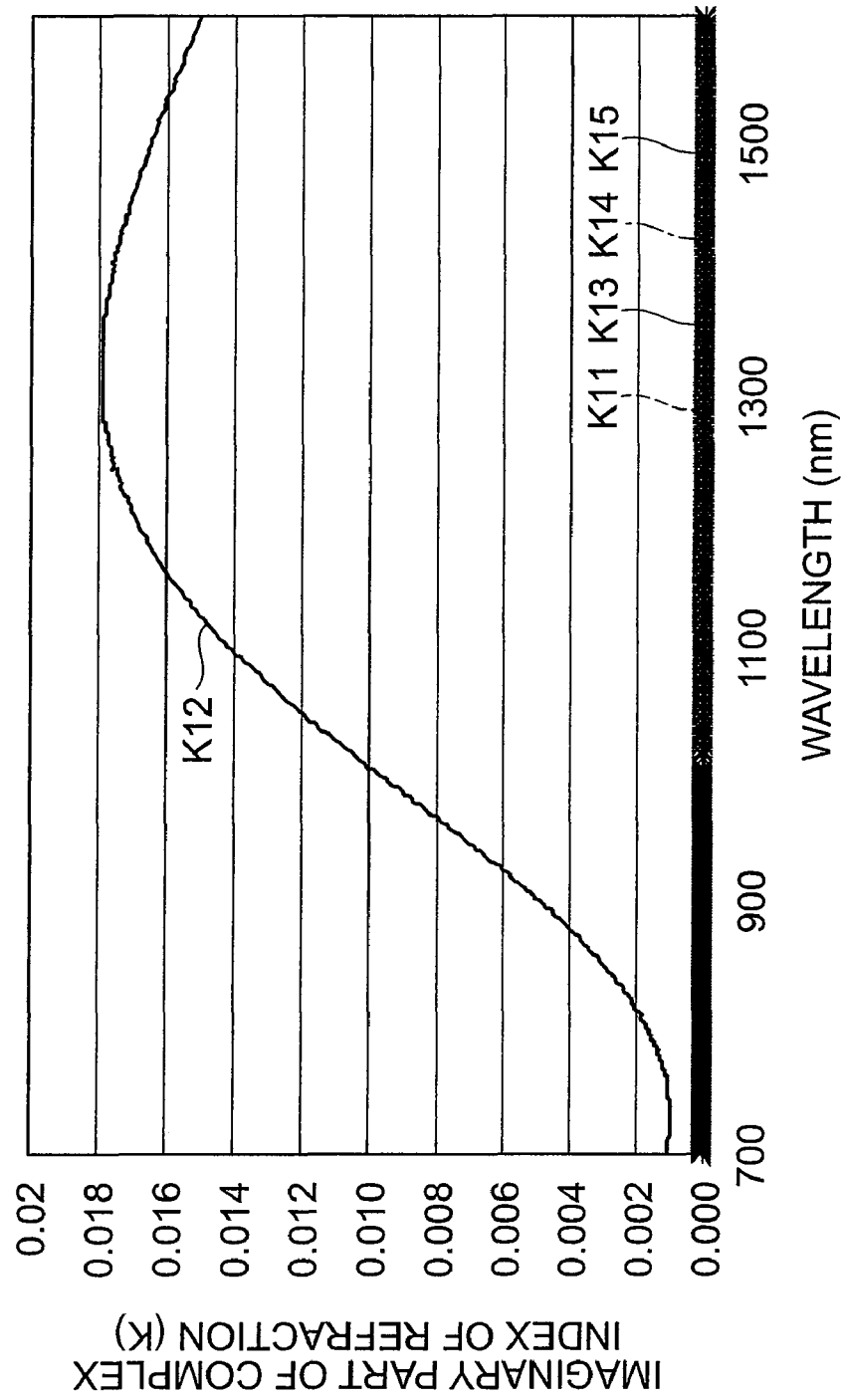
FIG. 10 is a graph showing part of spectra of the imaginary part K of the complex index of refraction obtained by spectroscopic ellipsometry measurement.

FIG. 10 is a graph showing part of spectra of the imaginary part K of the complex index of refraction obtained by the spectroscopic ellipsometry measurement. The spectra K11 to K15 in the graph indicate spectra in the wavelength range of 700 to 1600 nm of the imaginary part K of the complex index of refraction of the monocrystalline GaN substrates of Experiment Example 1 to Experiment Example 5, respectively. As shown in the graph, the spectrum K12 only had a peak, and the spectra K11, K13 to K15 had the value of zero. It was thus found that the spectroscopic ellipsometry measurement of the monocrystalline GaN substrate with a high level of damage provided nonzero values of the imaginary part K of the complex index of refraction in the wavelength range of 700 to 1600 nm.

Figure 11:
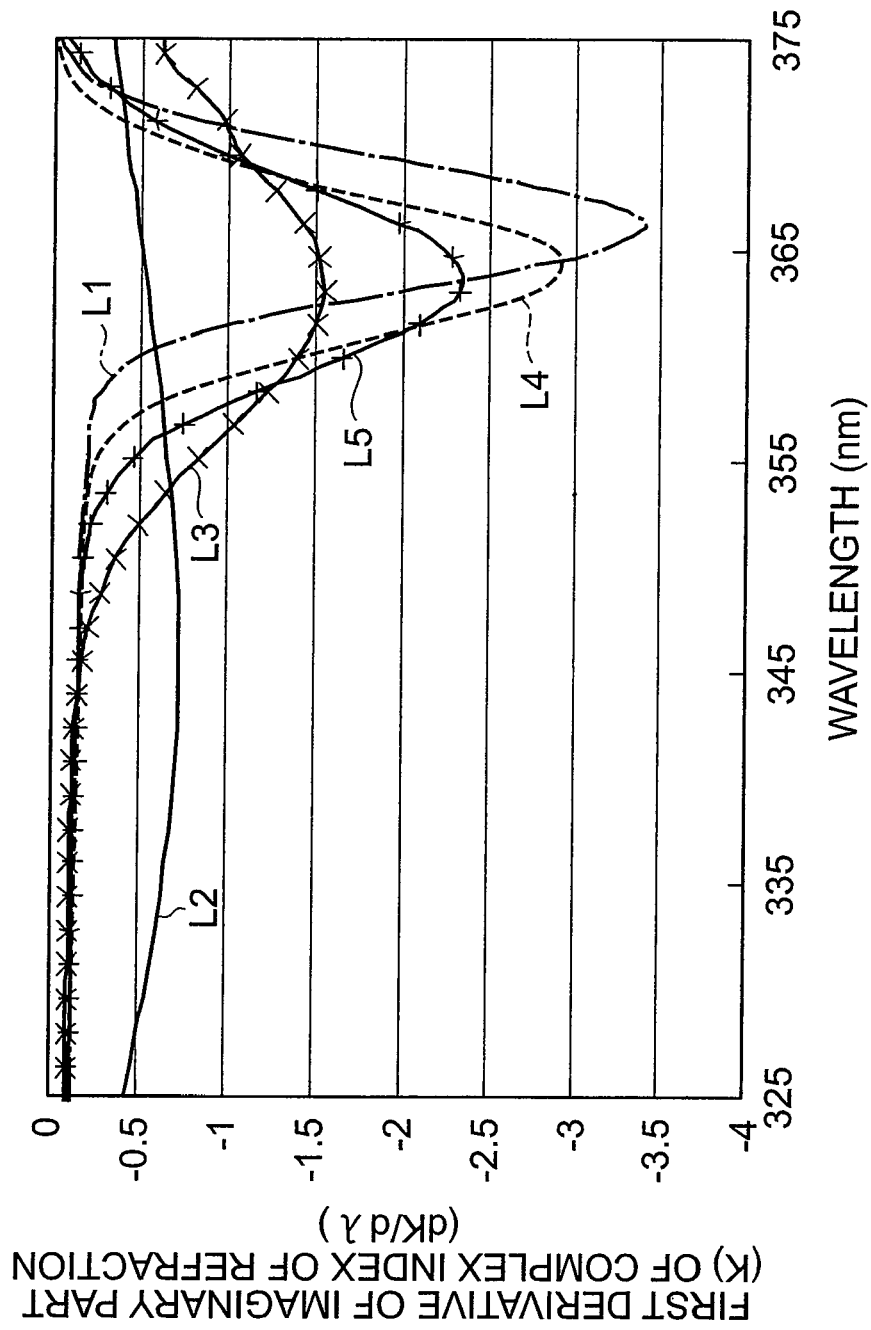
FIG. 11 is a graph showing first derivatives of spectra K1 to K5 shown in FIG. 9.

FIG. 11 is a graph showing the first derivatives of the spectra K1 to K5 shown in FIG. 9. Specifically, the imaginary part K of the complex index of refraction was differentiated with respect to wavelength. Spectra L1 to L5 indicating the first derivatives in the graph represent the first derivatives of the spectra K1 to K5 (slopes of spectra K1 to K5), respectively. As shown in the graph, each of the spectra L1 to L5 has an extremum. It was found that with increasing level of damage, the absolute value of the extremum (the maximum absolute value of the slope of spectra K1 to K5) tended to decrease and the wavelength at the extremum tended to decrease.

In the spectra L2, L3, the wavelengths at which the absolute value of the slope of the spectrum in the wavelength band of 300 to 400 nm was maximum, were 347 nm and 361 nm, respectively.

Figure 12:
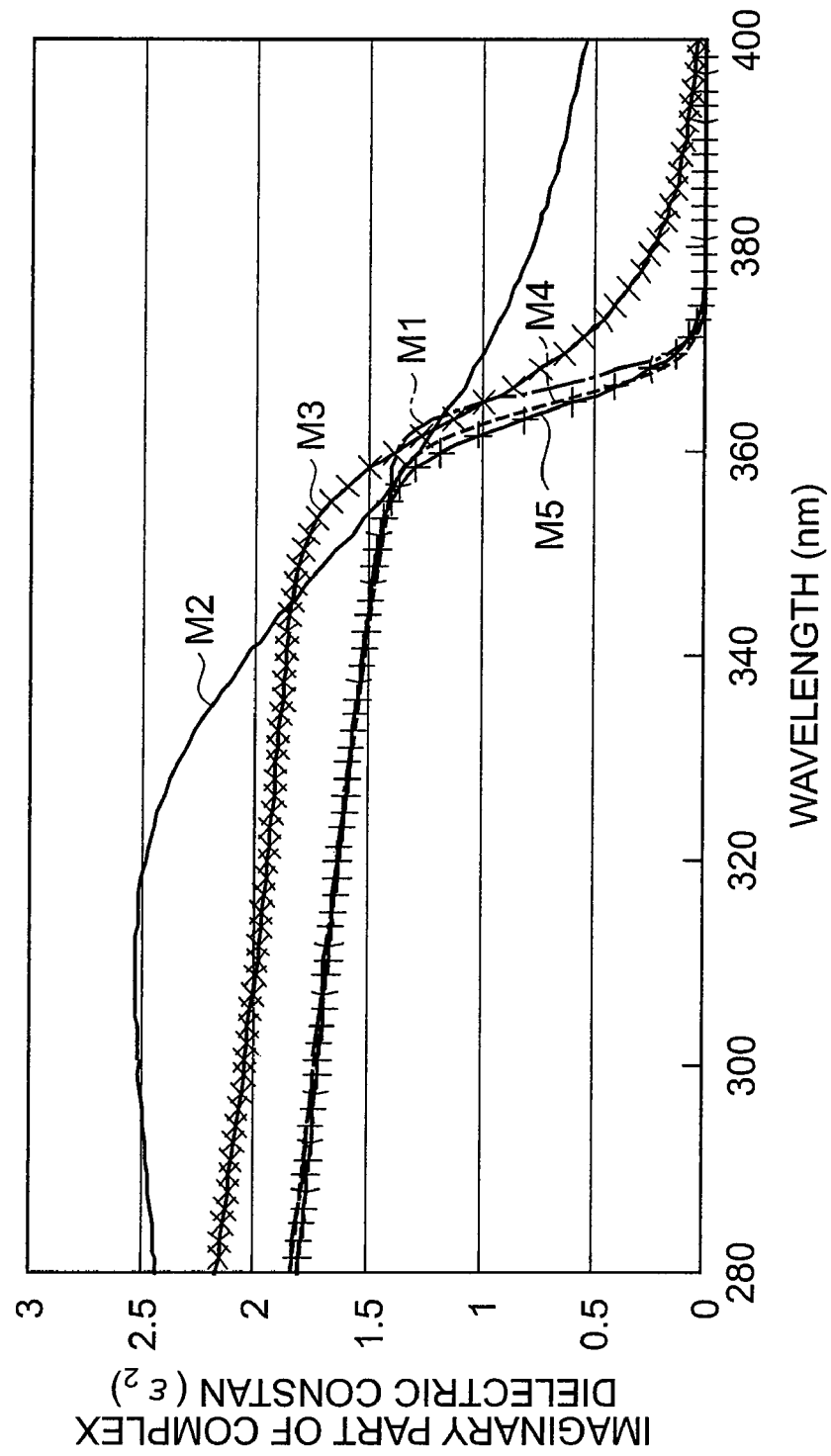
FIG. 12 is a graph showing part of spectra of the imaginary part $\in_2$ of the complex dielectric constant obtained by spectroscopic ellipsometry measurement.

FIG. 12 is a graph showing part of spectra of the imaginary part $\in_2$ of the complex dielectric constant obtained by spectroscopic ellipsometry measurement. Spectra M1 to M5 in the graph represent spectra in the wavelength band of 280 to 400 nm of the imaginary part $\in_2$ of the complex dielectric constant of the monocrystalline GaN substrates of Experiment Example 1 to Experiment Example 5, respectively. It was found from the graph that the spectra M1 to M5 had a spread on the longer wavelength side and on the shorter wavelength side than 365 nm. It was also found that with increasing level of damage, values of the imaginary part 82 of the complex dielectric constant on the longer wavelength side and on the shorter wavelength side than 365 nm tended to increase.

In the spectra M1, M4, M5, M3, and M2, absolute values of the difference between the imaginary part $\in_2$ of the complex dielectric constant at 360 nm and the imaginary part $\in_2$ of the complex dielectric constant at 370 nm were 1.2, 1.195, 1.048, 0.759, and 0.235, respectively. In the spectra M1, M4, M5, M3, and M2, absolute values of the imaginary part $\in_2$ of the complex dielectric constant at 370 nm were 0.13, 0.16, 0.63, 0.73, and 1.00, respectively.

Figure 13:
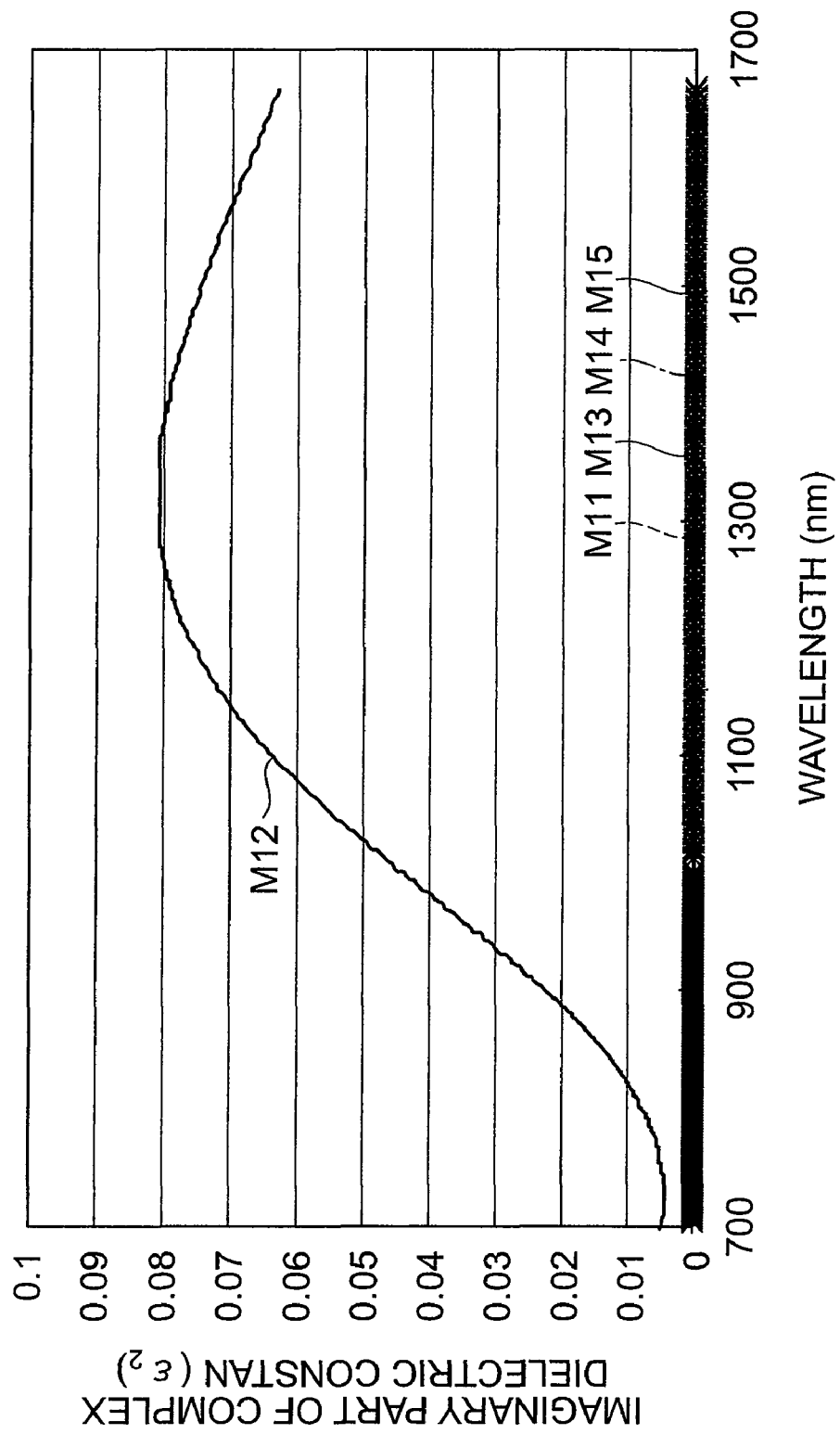
FIG. 13 is a graph showing portions located on the longer wavelength side of spectra M1 to M5 shown in FIG. 12.

FIG. 13 is a graph showing part of spectra of the imaginary part $\in_2$ of the complex dielectric constant obtained by spectroscopic ellipsometry measurement. Spectra M11 to M15 in the graph represent spectra in the wavelength band of 700 to 1700 nm of the imaginary part $\in_2$ of the complex dielectric constant of the monocrystalline GaN substrates of Experiment Example 1 to Experiment Example 5, respectively. As shown in the graph, the spectrum M12 only had a peak, and the spectra M11, M13 to M15 had the value of zero. It was thus found that the spectroscopic ellipsometry measurement of the monocrystalline GaN substrate with a high level of damage provided nonzero values of the imaginary part $\in_2$ of the complex dielectric constant in the wavelength band of 700 to 1700 nm.

Figure 14:
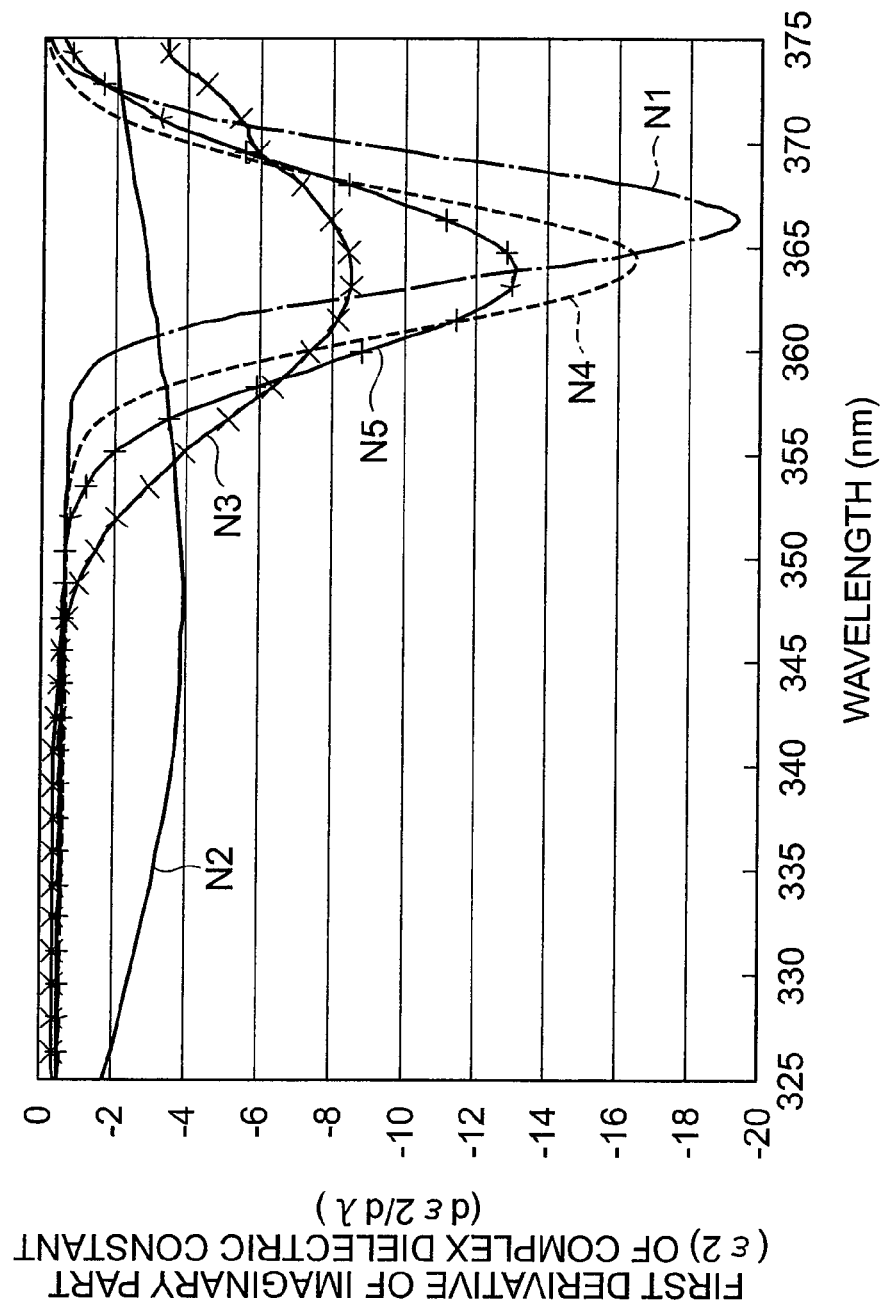
FIG. 14 is a graph showing first derivatives of spectra M1 to M5 shown in FIG. 12.

FIG. 14 is a graph showing the first derivatives of the spectra M1 to M5 shown in FIG. 12. Specifically, the imaginary part $\in_2$ of the complex dielectric constant was differentiated with respect to wavelength. The spectra N1 to N5 showing the first derivatives in the graph indicate the first derivatives of the spectra M1 to M5 (slopes of spectra M1 to M5), respectively. As shown in the graph, each of the spectra N1 to N5 has an extremum. It was also found that with increasing level of damage, the absolute value of the extremum (the maximum absolute value of the slope of spectra M1 to M5) tended to decrease and the wavelength at the extremum tended to decrease.

In the spectra N2, N3, the wavelengths at which the absolute value of the slope of the spectrum in the wavelength band of 300 to 400 nm was maximum, were 347 nm and 363 nm, respectively.

Figure 15:
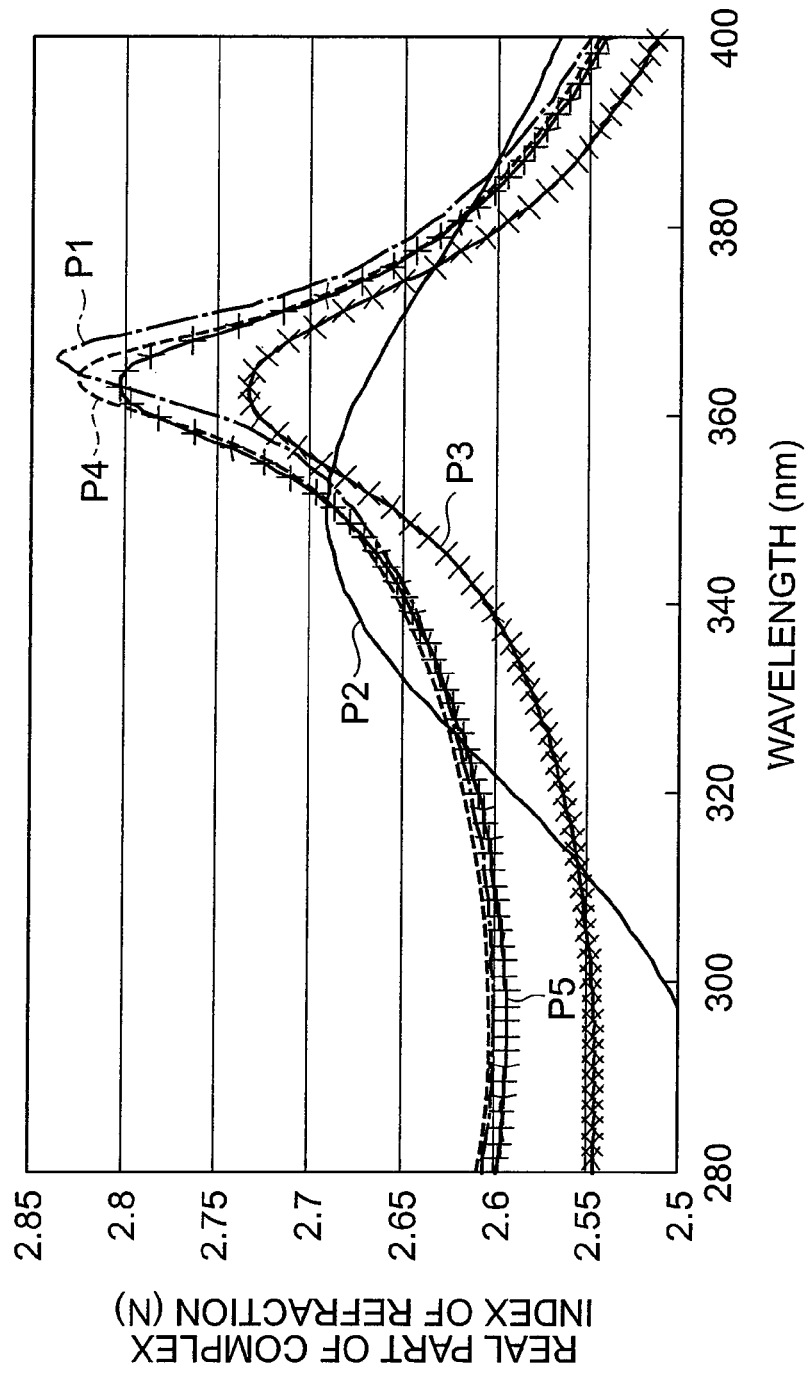
FIG. 15 is a graph showing part of spectra of the real part N of the complex index of refraction obtained by spectroscopic ellipsometry measurement.

FIG. 15 is a graph showing part of spectra of the real part N of the complex index of refraction obtained by spectroscopic ellipsometry measurement. Spectra P1 to P5 in the graph show spectra in the wavelength band of 280 to 400 nm of the real part N of the complex index of refraction of the monocrystalline GaN substrates of Experiment Example 1 to Experiment Example 5, respectively. It was found from the graph that with increasing level of damage, the maximum of spectra P1 to P5 tended to decrease, the wavelength at the maximum tended to decrease, and the half width of the peak tended to increase.

In the spectra P1, P4, P5, P3, and P2, absolute values of the difference between the real part N of the complex index of refraction at 365 nm and the real part N of the complex index of refraction at 375 nm were 0.15, 0.134, 0.126, 0.08, and 0.029, respectively. In the spectra P2 and P3, maxima of the spectra in the wavelength band of 300 to 400 nm were 2.69 and 2.733, respectively.

Figure 16:
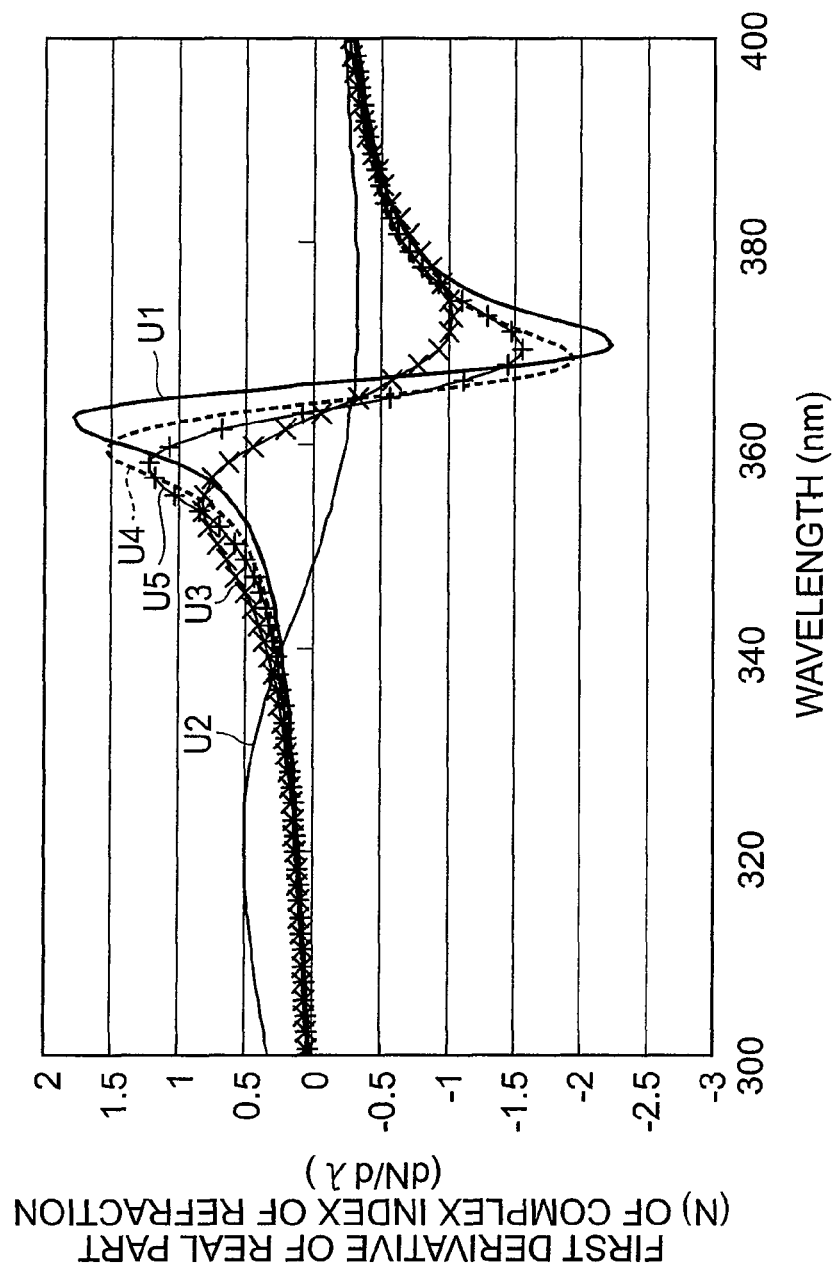
FIG. 16 is a graph showing first derivatives of spectra P1 to P5 shown in FIG. 15.

FIG. 16 is a graph showing the first derivatives of the spectra P1 to P5 shown in FIG. 15. Specifically, the real part N of the complex index of refraction was differentiated with respect to wavelength. Spectra U1 to U5 showing the first derivatives in the graph represent the first derivatives of the spectra P1 to P5 (slopes of spectra P1 to P5), respectively. As shown in the graph, the spectra U1 to U5 have a maximum in a portion located on the shorter wavelength side than the wavelength where the value of the first derivative is zero. It was found from this fact that in the portion located on the shorter wavelength side than the wavelength where the value of the first derivative was zero, the absolute value of the extremum (the maximum absolute value of the slope of spectra P1 to P5) tended to decrease and the wavelength at the extremum tended to decrease, with increasing level of damage.

The spectra U1 to U5 have a minimum in a portion located on the longer wavelength side than the wavelength where the value of the first derivative is zero. It was found from this fact that in the portion located on the longer wavelength side than the wavelength where the value of the first derivative was zero, the absolute value of the extremum (the maximum absolute value of the slope of spectra P1 to P5) decreased with increasing level of damage.

Figure 17:
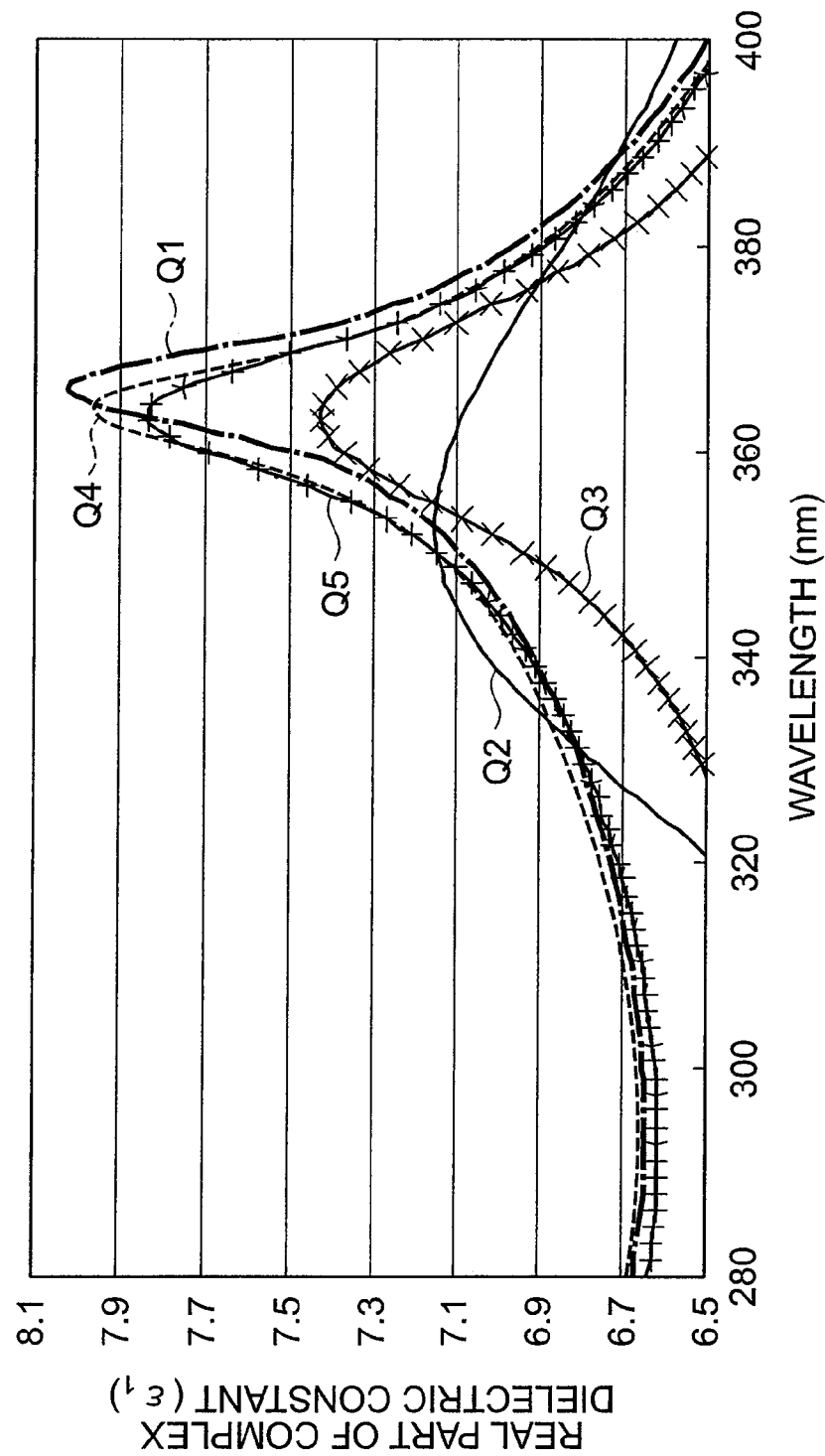
FIG. 17 is a graph showing part of spectra of the real part $\in_1$ of the complex dielectric constant obtained by spectroscopic ellipsometry measurement.

FIG. 17 is a graph showing part of spectra of the real part $\in_1$ of the complex dielectric constant obtained by spectroscopic ellipsometry measurement. Spectra Q1 to Q5 in the graph represent spectra in the wavelength band of 280 to 400 nm of the real part $\in_1$ of the complex dielectric constant of the monocrystalline GaN substrates of Experiment Example 1 to Experiment Example 5, respectively. It was found from the graph that with increasing level of damage, the maximum of spectra Q1 to Q5 tended to decrease, the wavelength at the maximum tended to decrease, and the half width of the peak tended to increase.

In the spectra Q2, Q3, Q5, Q4, and Q1, absolute values of the difference between the real part $\in_1$ of the complex dielectric constant at 365 nm and the real part $\in_1$ of the complex dielectric constant at 375 nm were 0.125, 0.326, 0.416, 0.589, and 0.69, respectively. In the spectra Q2 and Q3, maxima of spectra in the wavelength band of 300 to 400 nm were 7.15 and 7.43, respectively.

Figure 18:
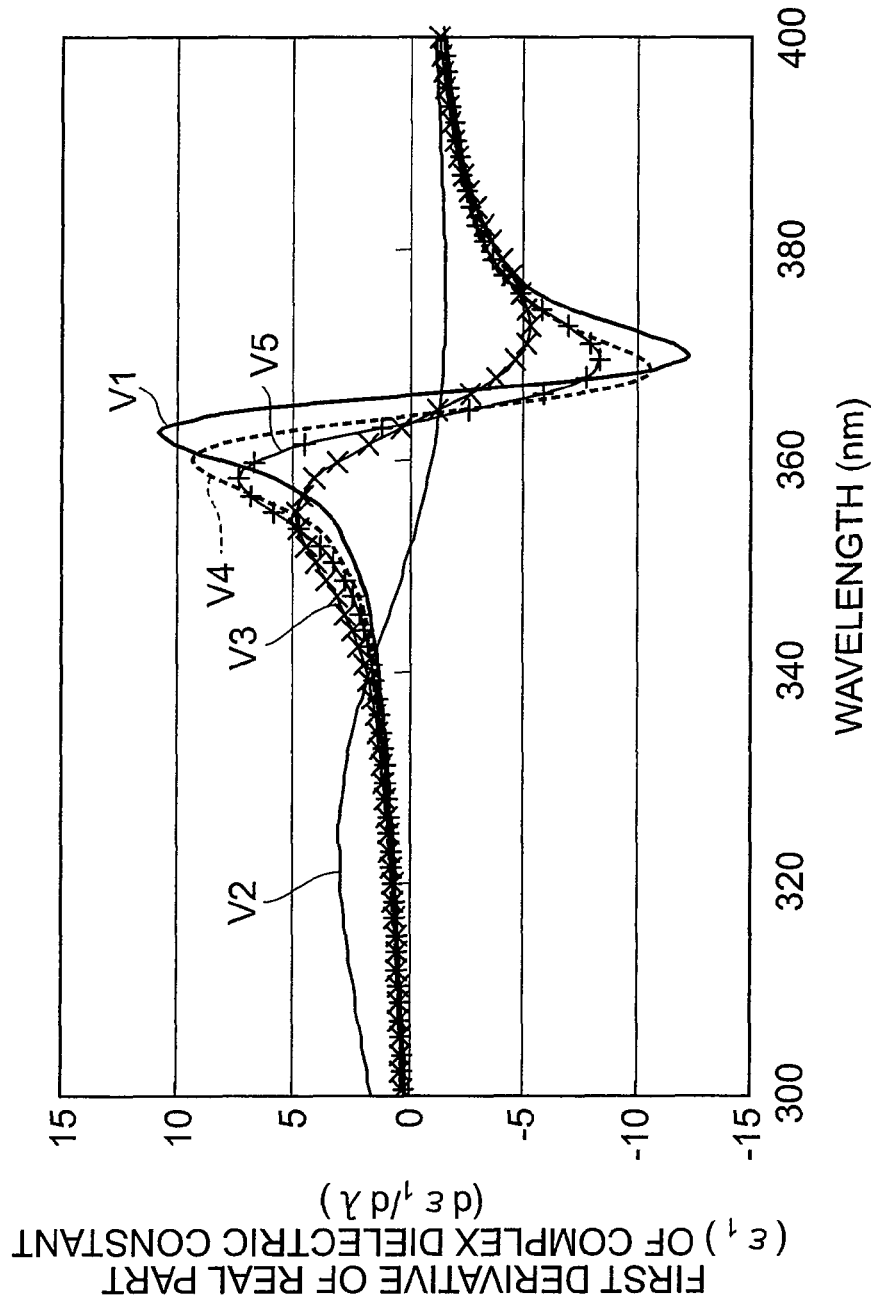
FIG. 18 is a graph showing first derivatives of spectra Q1 to Q5 shown in FIG. 17.

FIG. 18 is a graph showing the first derivatives of the spectra Q1 to Q5 shown in FIG. 17. Specifically, the real part $\in_1$ of the complex dielectric constant was differentiated with respect to wavelength. Spectra V1 to V5 showing the first derivatives in the graph represent the first derivatives of the spectra Q1 to Q5 (slopes of spectra Q1 to Q5), respectively. As shown in the graph, each of the spectra V1 to V5 has a maximum in a portion located on the shorter wavelength side than the wavelength where the value of the first derivative is zero. It was found from this fact that in the portion located on the shorter wavelength side than the wavelength where the value of the first derivative was zero, the absolute value of the extremum (the maximum absolute value of the slope of spectra Q1 to Q5) tended to decrease and the wavelength at the extremum tended to decrease, with increasing level of damage.

Each of the spectra V1 to V5 has a minimum in a portion located on the longer wavelength side than the wavelength where the value of the first derivative is zero. It was found from this fact that in the portion located on the longer wavelength side than the wavelength where the value of the first derivative was zero, the absolute value of the extremum (the maximum absolute value of the slope of spectra Q1 to Q5) decreased with increasing level of damage.

Figure 19:
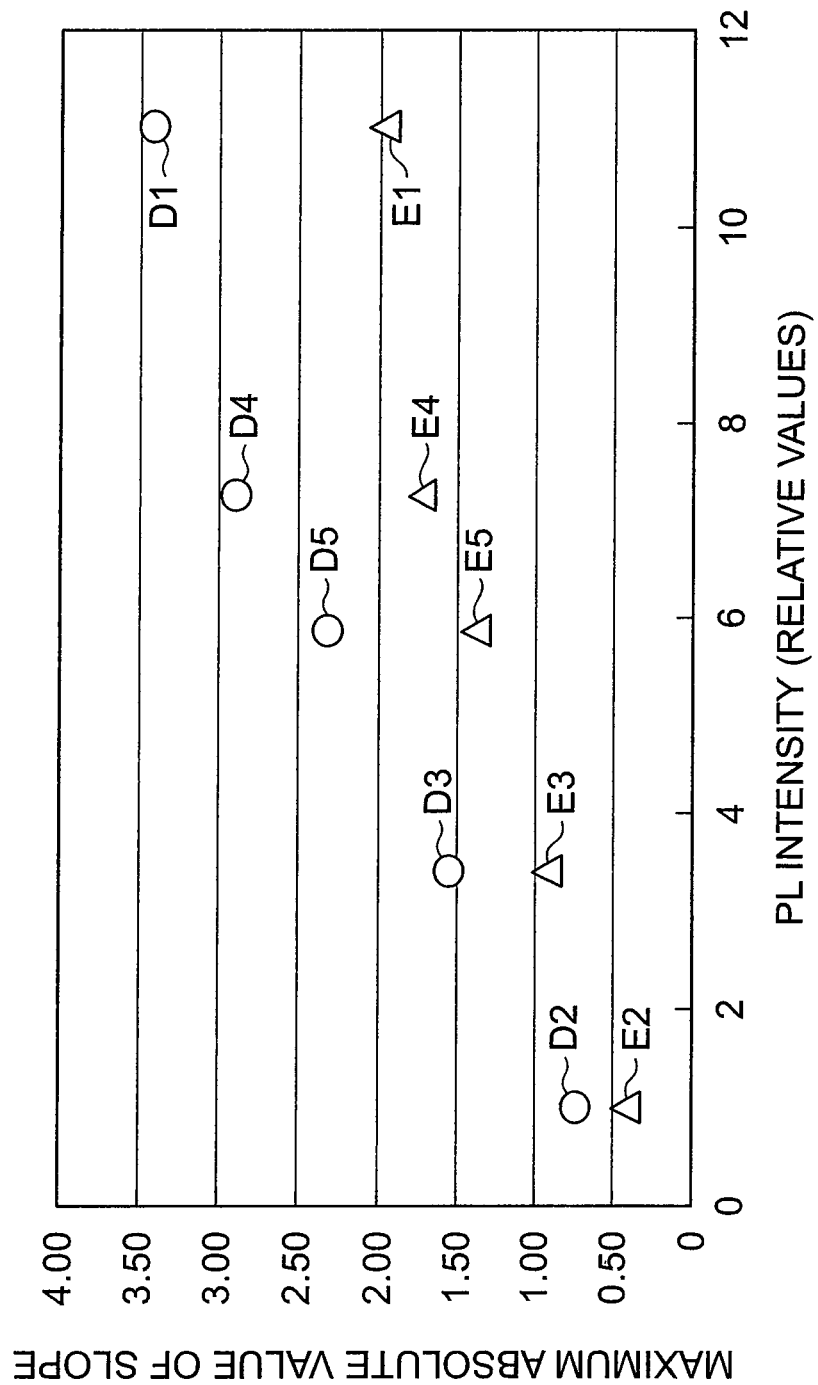
FIG. 19 is a graph showing a relation between PL intensities shown in FIG. 8, and maximum absolute values of slopes of spectra of the imaginary part K of the complex index of refraction and the real part N of the complex index of refraction.

FIG. 19 is a graph showing a relation between the PL intensities shown in FIG. 8, and maximum absolute values of the slopes of the spectra of the imaginary part K of the complex index of refraction and the real part N of the complex index of refraction. Plots D1 to D5 in the graph represent maximum absolute values $G1_{max}$ of the slopes of the spectra K1 to K5 shown in FIG. 9 (absolute values of extrema of the spectra L1 to L5 shown in FIG. 11), respectively. Plots E1 to E5 represent maximum absolute values $G3_{max}$ of the slopes of the spectra P1 to P5 shown in FIG. 15, respectively. It was found from the graph that with increasing level of damage, the values of plots D1 to D5, E1 to E5 tended to decrease. It was thus found that with increasing level of damage, the maximum absolute values $G3_{max}$ of the slopes of spectra P1 to P5 shown in FIG. 15 decreased.

Figure 20:
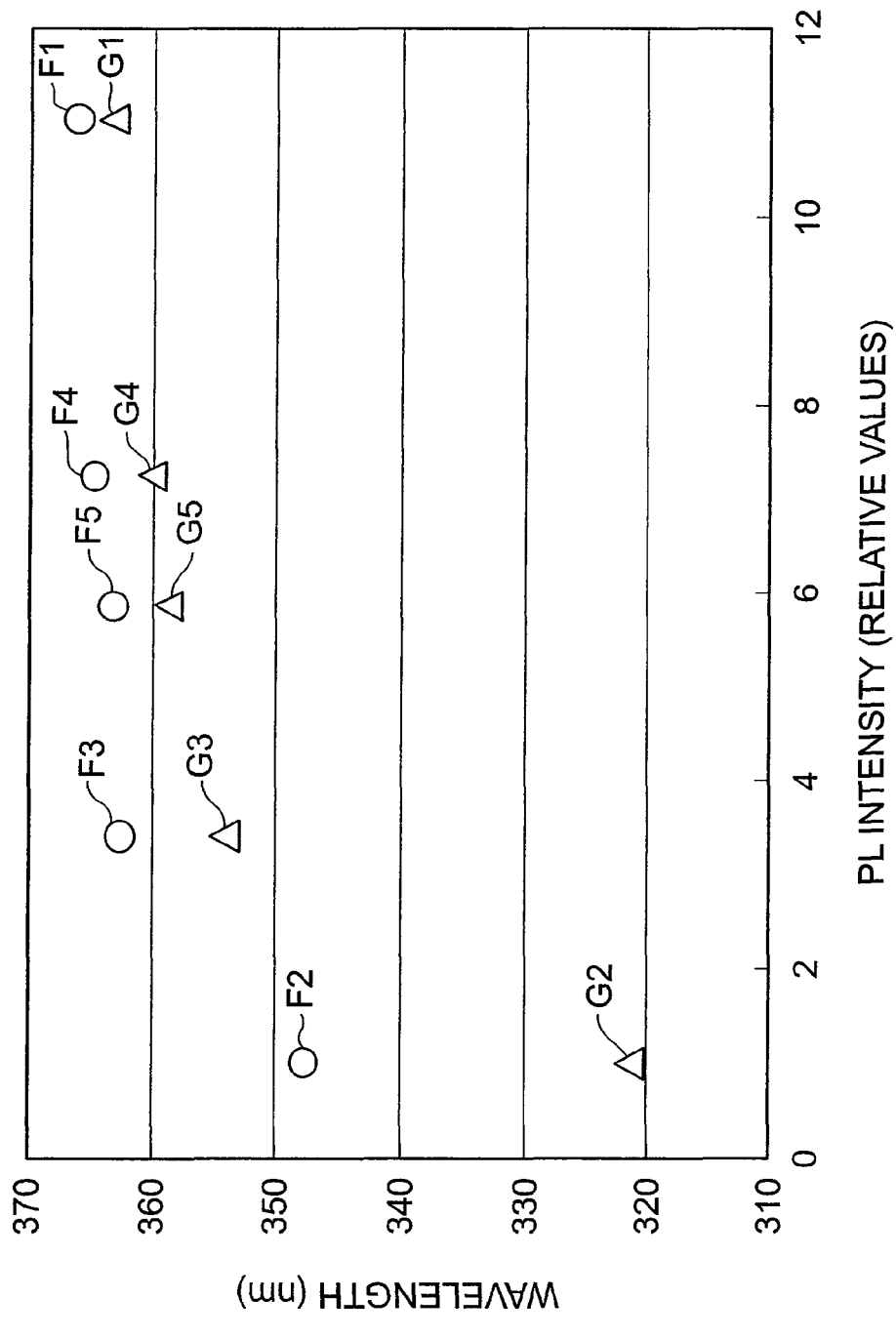
FIG. 20 is a graph showing a relation between PL intensities shown in FIG. 8, and wavelengths to achieve maximum absolute values of slopes of spectra of the imaginary part K of the complex index of refraction and the real part N of the complex index of refraction.

FIG. 20 is a graph showing a relation between the PL intensities shown in FIG. 8, and wavelengths where the absolute values of the slopes of the spectra of the imaginary part K of the complex index of refraction and the real part N of the complex index of refraction are maximum. Plots F1 to F5 in the graph represent wavelengths at the maximum absolute value of the slopes of the spectra K1 to K5 shown in FIG. 9 (wavelengths of extrema of spectra L1 to L5 shown in FIG. 11), respectively. In addition, plots G1 to G5 represent wavelengths at the maximum absolute value of the slope (first derivative) in the portion located on the shorter wavelength side than the wavelength corresponding to the maximum in the spectra P1 to P5 shown in FIG. 15, respectively. It was found from the graph that with increasing level of damage, the values of plots F1 to F5, G1 to G5 tended to decrease.

Next, Table 1 presents the thickness of the mixed layer in the model structure of the monocrystalline GaN substrate. It was found from Table 1 that the thickness of the mixed layer increased with increasing level of damage.

TABLE 1

|  | Thickness of Mixed Layer[nm] |
| --- | --- |
| Experiment Example 2 | 7.2 |
| Experiment Example 3 | 3.8 |
| Experiment Example 5 | 1.6 |
| Experiment Example 4 | 1.1 |
| Experiment Example 1 | 0.7 |

Experiment Example 6

A monocrystalline GaN substrate obtained in the same manner as in Experiment Example 1 was cleaned with HCl solution and 50% NH$_4$OH to obtain a monocrystalline GaN substrate of Experiment Example 6.

Experiment Example 7

A monocrystalline GaN substrate obtained in the same manner as in Experiment Example 6 was cleaned with a solution as a 1:1 mixture of 50% NH$_4$OH and hydrogen peroxide to obtain a monocrystalline GaN substrate of Experiment Example 7. The spectroscopic ellipsometry measurement was carried out in the same manner as in Experiment Example 1 to Experiment Example 5, for each of surfaces of the monocrystalline GaN substrates of Experiment Examples 6, 7.

Figure 21:
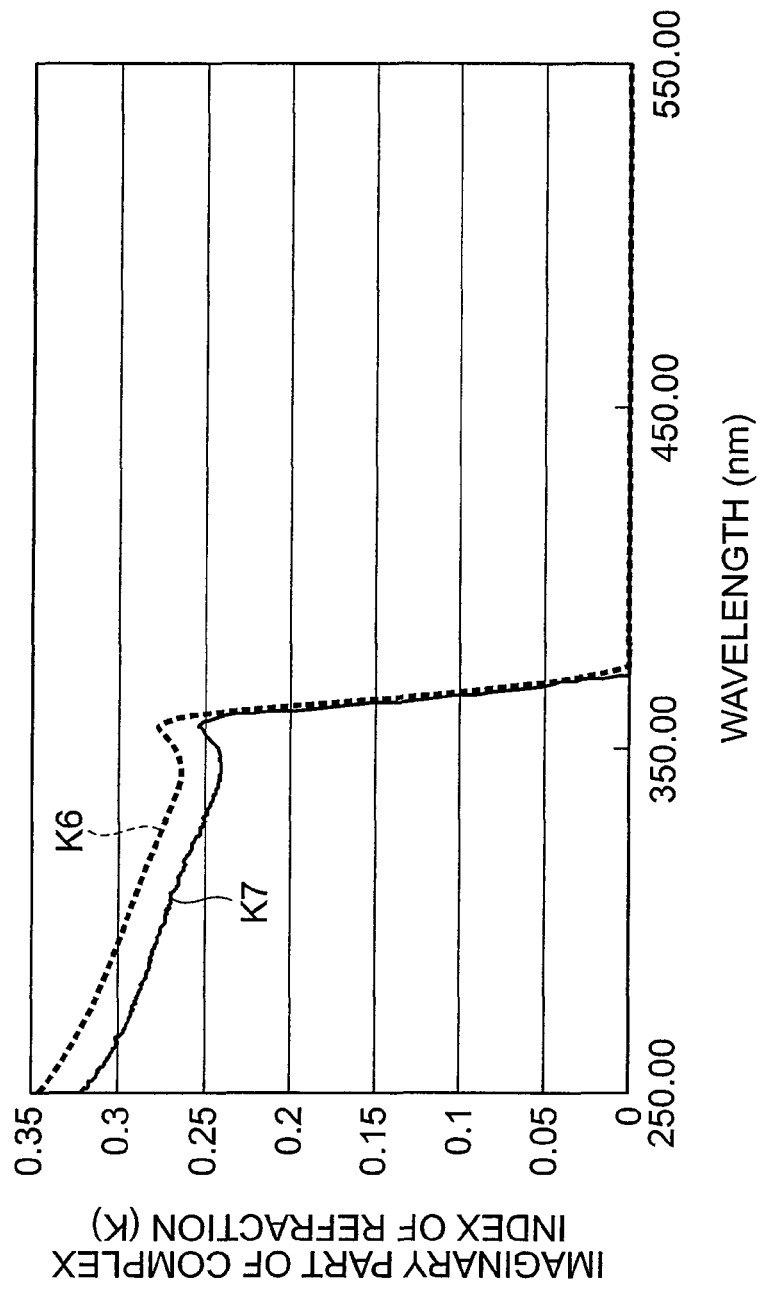
FIG. 21 is a graph showing part of spectra of the imaginary part K of the complex index of refraction obtained by spectroscopic ellipsometry measurement.

FIG. 21 is a graph showing part of spectra of the imaginary part K of the complex index of refraction obtained by the spectroscopic ellipsometry measurement. Spectra K6, K7 in the graph represent spectra in the wavelength band of 250 to 550 nm of the imaginary part K of the complex index of refraction of the monocrystalline GaN substrates of Experiment Examples 6, 7, respectively. A maximum was observed near 365 nm in the graph. A conceivable reason for it is that repetitions of cleaning decreased the level of damage to facilitate generation of exciton.

Experiment Example 8

A surface of a monocrystalline InP substrate with the diameter of 3 inches having the (110) face as a principal surface was polished to be mirror-finished, thereby obtaining a monocrystalline InP substrate of Experiment Example 8.

Experiment Example 9

A monocrystalline InP substrate of Experiment Example 9 was obtained in the same manner as in Experiment Example 8, except that dry etching by the reactive ion etching method was carried out, instead of the mirror finishing.

Experiment Example 10

A monocrystalline InP substrate obtained in the same manner as in Experiment Example 9 was subjected to wet etching, thereby obtaining a monocrystalline InP substrate of Experiment Example 10.

(Cathodoluminescence Intensity Measurement)

Cathodoluminescence intensity measurement was carried out for the monocrystalline InP substrates of Experiment Example 8, Experiment Example 9, and Experiment Example 10. The measurement results are presented in Table 2. The cathode luminescence intensities are relative values, based on the cathodoluminescence intensity of the monocrystalline InP substrate of Experiment Example 8 being defined as 1. The cathodoluminescence intensities are values obtained by integrating an intensity distribution near the wavelength of 900 nm within a field of view at the magnification of 10000.

TABLE 2

| | Cathodoluminescence Intensity (Relative Intensity) |
|---|---|
| Experiment Example 8 | 1.00 |
| Experiment Example 9 | 1.18 |
| Experiment Example 10 | 1.26 |

It was found from Table 2 that the level of damage tended to decrease in the order of Experiment Example 8, Experiment Example 9, and Experiment Example 10.

(Spectroscopic Ellipsometry Measurement)

The spectroscopic ellipsometry measurement was carried out for surfaces of the monocrystalline InP substrates of Experiment Example 8, Experiment Example 9, and Experiment Example 10. The spectroscopic ellipsometer 16 used was the spectroscopic ellipsometer available from SOPRA Co. The angle of incidence of the light LT1 was set at 75° to achieve high measurement sensitivity. The measurement wavelength range was 300 to 1200 nm.

(Damage Evaluation)

The model structure of the monocrystalline InP substrate was a monocrystalline InP substrate having a damage layer as a surface layer. Furthermore, a mixed layer of an oxide film and an uneven layer was assumed on the damage layer. The mixed layer was assumed to be a layer as a mixture of oxide and air 50% each by effective medium approximation. Optical simulation and fitting were conducted using this model structure. They resulted in obtaining the spectrum of the real part $\in_1$ of the complex dielectric constant, the spectrum of the imaginary part $\in_2$ of the complex dielectric constant, the spectrum of the real part N of the complex index of refraction, and the spectrum of the imaginary part K of the complex index of refraction.

Figure 22:
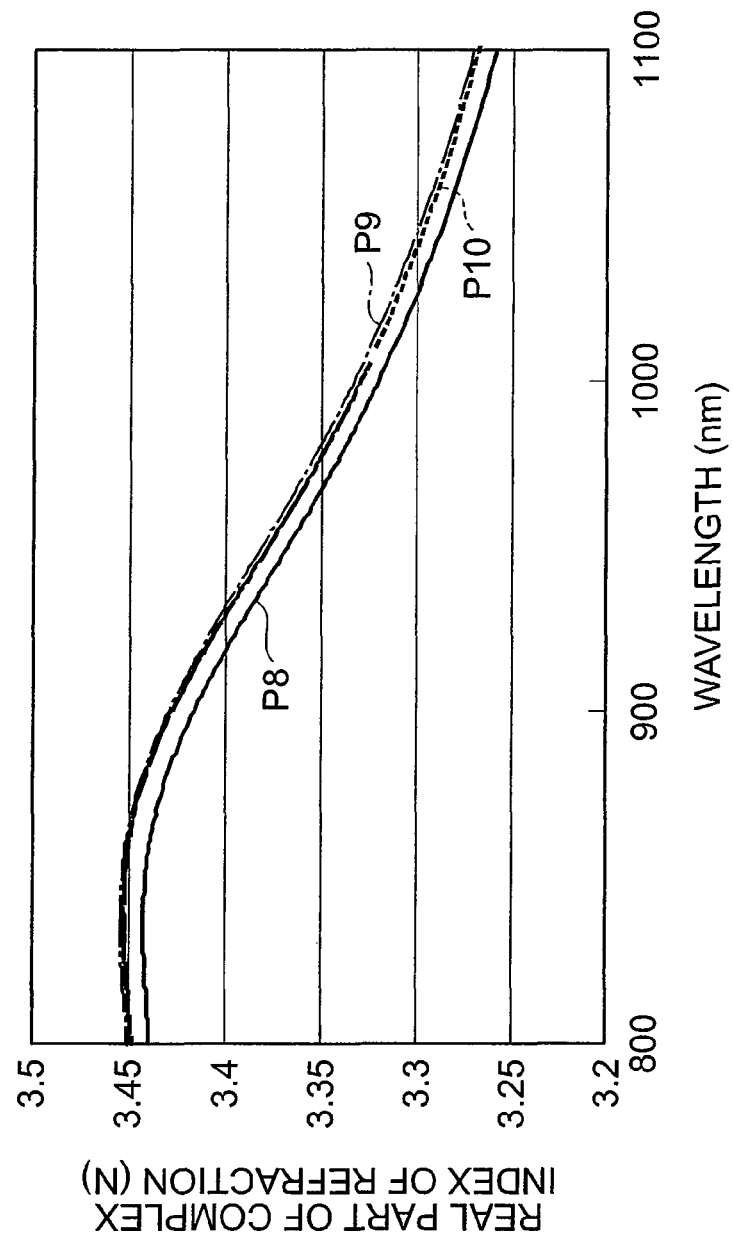
FIG. 22 is a graph showing part of spectra of the real part N of the complex index of refraction obtained by spectroscopic ellipsometry measurement.

FIG. 22 is a graph showing part of spectra of the real part N of the complex index of refraction obtained by the spectroscopic ellipsometry measurement. Spectra P8 to P10 in the graph represent spectra in the wavelength band of 800 to 1100 nm of the real part N of the complex index of refraction of the monocrystalline InP substrates of Experiment Example 8 to Experiment Example 10, respectively.

Figure 23:
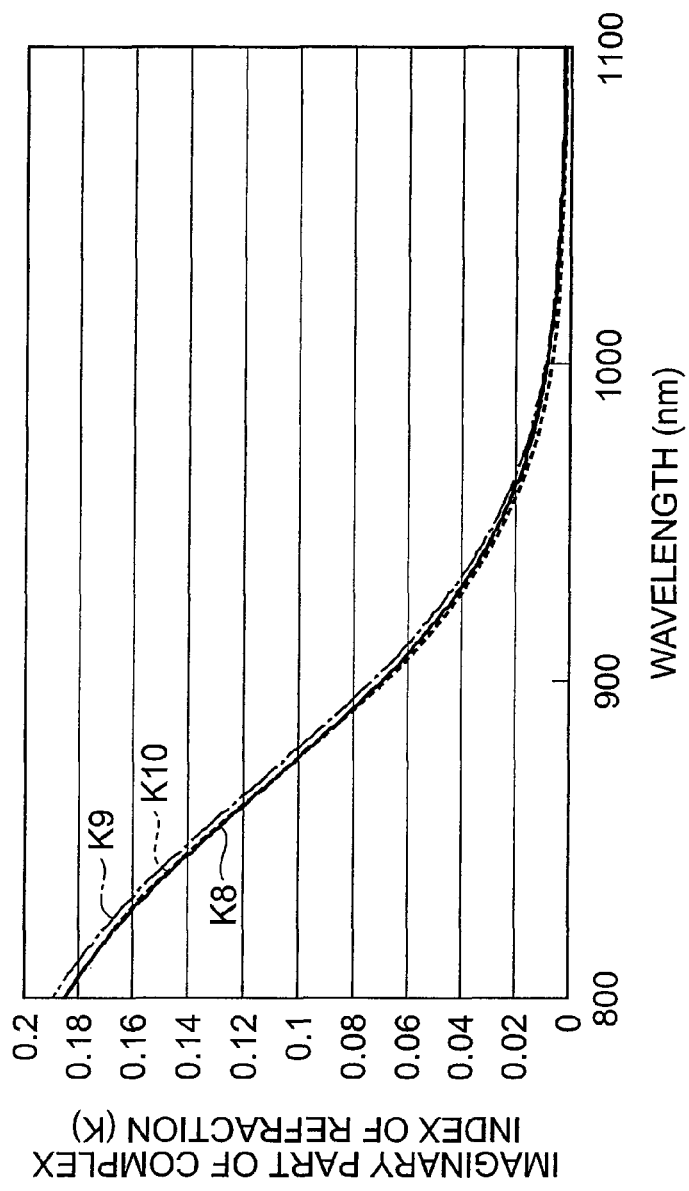
FIG. 23 is a graph showing part of spectra of the imaginary part K of the complex index of refraction obtained by spectroscopic ellipsometry measurement.

FIG. 23 is a graph showing part of spectra of the imaginary part K of the complex index of refraction obtained by the spectroscopic ellipsometry measurement. Spectra K8 to K10 in the graph represent spectra in the wavelength band of 800 to 1100 nm of the imaginary part K of the complex index of refraction of the monocrystalline InP substrates of Experiment Example 8 to Experiment Example 10, respectively.

Figure 24:
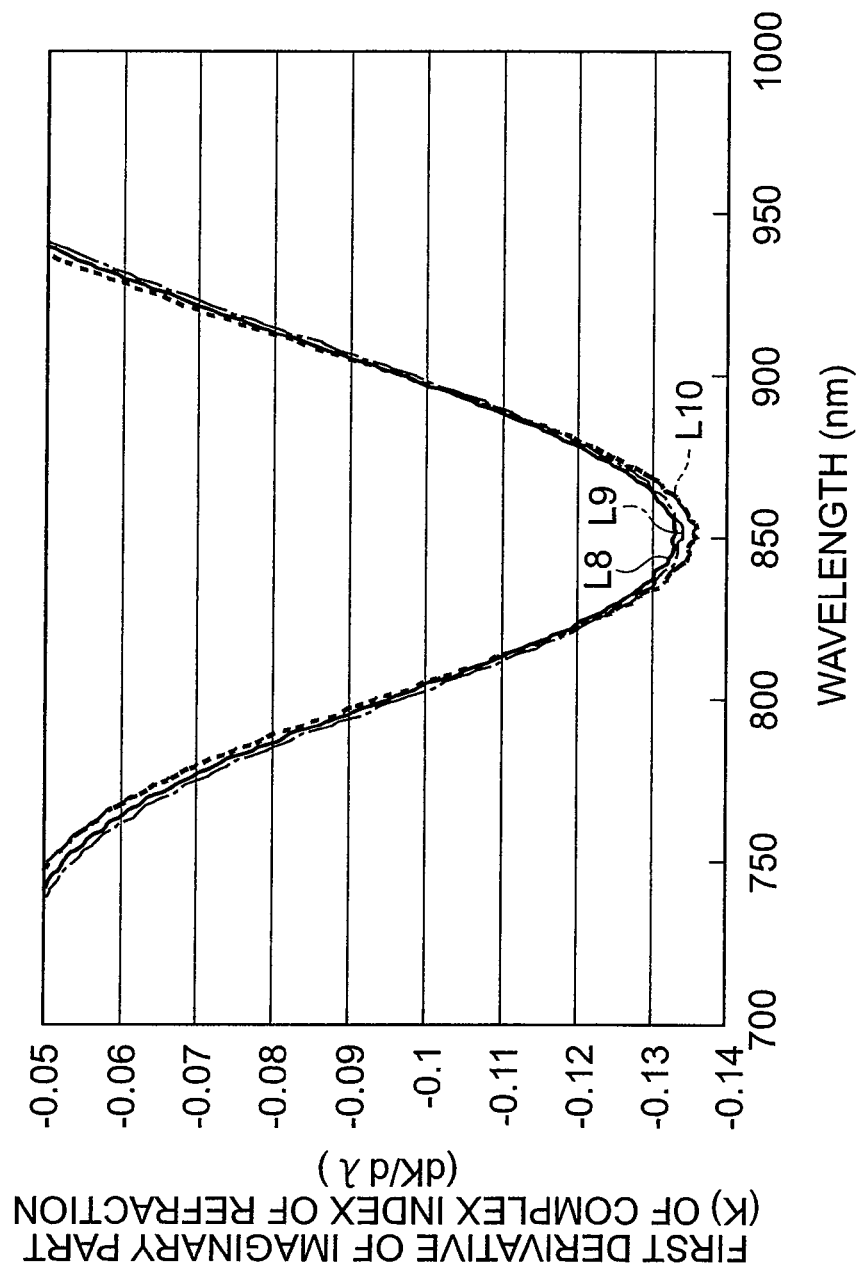
FIG. 24 is a graph showing first derivatives of spectra P8 to P10 shown in FIG. 22.

FIG. 24 is a graph showing the first derivatives of the spectra P8 to P10 shown in FIG. 22. Specifically, the imaginary part K of the complex index of refraction was differentiated with respect to wavelength. Spectra L8 to L10 showing the first derivatives in the graph represent the first derivatives of the spectra K8 to K10, respectively. As shown in the graph, each of the spectra L8 to L10 has an extremum. It was found that with increasing level of damage, the absolute value of the extremum (the maximum absolute value of the slope of spectra P8 to P10) tended to decrease and the wavelength at the extremum tended to decrease.

FIG. 25 is a graph showing a relation between cathodoluminescence intensities and maximum absolute values of slopes. Plots H8 to H10 in the graph represent the maximum absolute values $G1_{max}$ of the slopes of the spectra K8 to K10 shown in FIG. 23 (absolute values of the extrema of the spectra L8 to L10 shown in FIG. 24), respectively. It was found from the graph that there was a correlation between the cathodoluminescence intensities and the maximum absolute values of the slopes and that the maximum absolute value of the slope tended to increase with decreasing level of damage.

Experiment Example 11

A monocrystalline GaN substrate of Experiment Example 11 without damage was prepared in the same manner as in Experiment Example 1, except that the substrate used was a monocrystalline GaN substrate 20 mm square.

Experiment Example 12

A monocrystalline GaN ingot was sliced to prepare a monocrystalline GaN substrate 20 mm square. The surface of the monocrystalline GaN substrate prepared was roughly polished and thereafter the surface was further polished with diamond abrasive grains having the grain size of 0.1 µm, thereby obtaining the monocrystalline GaN substrate of Experiment Example 12.

Experiment Example 13

A monocrystalline GaN substrate of Experiment Example 13 was prepared in the same manner as in Experiment Example 12, except that diamond abrasive grains with the grain size of 0.5 µm were used instead of the diamond abrasive grains with the grain size of 0.1 µm.

(Spectroscopic Ellipsometry Measurement)

Spectroscopic ellipsometry measurement was carried out for the surfaces of the monocrystalline GaN substrates of Experiment Example 11 to Experiment Example 13. The maximum absolute value $G1_{max}$ of the slope of the spectrum of the imaginary part K of the complex index of refraction was calculated for each of the monocrystalline GaN substrates of Experiment Example 11 to Experiment Example 13. The maximum $G1_{max}$ of Experiment Example 12 was 2.6 times the maximum $G1_{max}$ of Experiment Example 13. The maximum $G1_{max}$ of Experiment Example 11 was 2.9 times the maximum $G1_{max}$ of Experiment Example 13. This confirmed that the level of damage on the surface increased in the order of Experiment Example 11, Experiment Example 12, and Experiment Example 13.

Next, a thin film of GaN was formed in the film thickness of 1 µm by HVPE on the surfaces of the monocrystalline GaN substrates of Experiment Example 11 to Experiment Example 13. The conditions for forming a thin film of GaN were as follows. GaCl gas was obtained by reaction of Ga metal with HCl gas at 880° C.

Temperature of monocrystalline GaN substrate: 1000° C.
Reaction gases: $NH_3$ gas and GaCl gas
Pressure of $NH_3$ gas: 10 kPa
Pressure of GaCl gas: 0.6 Pa After formation of the GaN thin film, the surface roughness (Ra: arithmetic mean roughness) was measured for the GaN thin film by AFM. A percentage of lattice strain to the bulk was measured by X-ray diffraction. The measurement results of these are presented in Table 3. It was found from Table 3 that the monocrystalline GaN substrates of Experiment Example 11 and Experiment Example 12 had satisfactory performance as substrates to be used for the compound semiconductor devices.

TABLE 3

|  | Arithmetic Mean Roughness[nm] | Percentage of Lattice Strain[%] |
|---|---|---|
| Experiment Example 11 | 0.82 | 0.01 |
| Experiment Example 12 | 0.95 | 0.04 |
| Experiment Example 13 | 1.43 | 0.15 |

The present invention provides the damage evaluation methods of the compound semiconductor member and the production methods of the compound semiconductor member capable of highly accurately evaluating the level of damage on the surface and provides the gallium nitride compound semiconductor members and gallium nitride compound semiconductor membranes with a low level of damage.

What is claimed is:

1. A method of producing a compound semiconductor member, comprising:
    a step of performing spectroscopic ellipsometry measurement on a surface of the compound semiconductor member;
    a step of obtaining a spectrum of an imaginary part of a complex index of refraction from a measurement result of the spectroscopic ellipsometry measurement;
    a step of setting a wavelength range, the wavelength range including a wavelength corresponding to a bandgap of the compound semiconductor member;
    a step of obtaining a maximum slope of the spectrum in an absolute value within the wavelength range; and
    a step of determining that the compound semiconductor member is nondefective when the maximum slope of the spectrum in an absolute value is not less than a predetermined threshold.

2. The production method of the compound semiconductor member according to claim 1, wherein the compound semiconductor member is a compound semiconductor substrate.

3. The production method of the compound semiconductor member according to claim 1, wherein the compound semiconductor member is a compound semiconductor membrane provided on a substrate.

4. The production method of the compound semiconductor member according to claim 1, further comprising a step of forming a thin film on the surface of the compound semiconductor member, after the step of determining that the compound semiconductor member is nondefective.

5. The production method of the compound semiconductor member according to claim 1, further comprising a step of forming an electrode on the surface of the compound semiconductor member, after the step of determining that the compound semiconductor member is nondefective.

6. A method of producing a compound semiconductor member, comprising:
    a step of performing spectroscopic ellipsometry measurement on a surface of the compound semiconductor member;
    a step of obtaining a spectrum of an imaginary part of a complex index of refraction from a measurement result of the spectroscopic ellipsometry measurement;
    a step of setting a wavelength range, the wavelength range including a wavelength corresponding to a bandgap of the compound semiconductor member;
    a step of obtaining a wavelength at which a slope of the spectrum in an absolute value becomes maximum within the wavelength range; and
    a step of determining that the compound semiconductor member is nondefective when the wavelength obtained at the step of obtaining a wavelength is not less than a predetermined threshold.

* * * * *